US012421496B2

(12) United States Patent
Cho et al.

(10) Patent No.: US 12,421,496 B2
(45) Date of Patent: Sep. 23, 2025

(54) METHOD FOR PRODUCING NATURAL KILLER CELL AND USE THEREOF

(71) Applicant: KOREA RESEARCH INSTITUTE OF BIOSCIENCE AND BIOTECHNOLOGY, Daejeon (KR)

(72) Inventors: Yee Sook Cho, Daejeon (KR); Han-Seop Kim, Daejeon (KR); Binna Seol, Daejeon (KR); In Pyo Choi, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 666 days.

(21) Appl. No.: 16/649,417

(22) PCT Filed: Sep. 21, 2018

(86) PCT No.: PCT/KR2018/011247
§ 371 (c)(1),
(2) Date: Jul. 1, 2020

(87) PCT Pub. No.: WO2019/059713
PCT Pub. Date: Mar. 28, 2019

(65) Prior Publication Data
US 2020/0407685 A1    Dec. 31, 2020

(30) Foreign Application Priority Data

Sep. 21, 2017  (KR) .................. 10-2017-0121980
Sep. 20, 2018  (KR) .................. 10-2018-0113308

(51) Int. Cl.
   *C12N 5/0783*   (2010.01)
   *A61K 40/15*    (2025.01)
   *A61K 40/42*    (2025.01)
   *A61P 35/00*    (2006.01)

(52) U.S. Cl.
   CPC ............ *C12N 5/0646* (2013.01); *A61K 40/15* (2025.01); *A61K 40/42* (2025.01); *A61P 35/00* (2018.01); *C12N 5/0638* (2013.01); *A61K 2239/31* (2023.05); *A61K 2239/38* (2023.05); *A61K 2239/50* (2023.05); *C12N 2501/2307* (2013.01); *C12N 2501/2315* (2013.01); *C12N 2501/602* (2013.01); *C12N 2501/603* (2013.01); *C12N 2501/604* (2013.01); *C12N 2501/606* (2013.01); *C12N 2501/727* (2013.01)

(58) Field of Classification Search
   CPC ........ C12N 5/0646; A61P 35/00; A61K 35/17
   See application file for complete search history.

(56) References Cited

U.S. PATENT DOCUMENTS

| 8,822,218  | B2 * | 9/2014 | Kimbrel   | C12N 5/0639 |
|            |      |        |           | 435/325     |
| 9,260,696  | B2 * | 2/2016 | Kaufman   | A61P 31/20  |
| 10,947,502 | B2 * | 3/2021 | Vodyanyk  | C12N 5/0635 |
| 2014/0023626 | A1 | 1/2014 | Peled et al. |      |

FOREIGN PATENT DOCUMENTS

| KR | 10-2015-0015294 A |   | 2/2015  |             |
| KR | 10-2015-0087727 A |   | 7/2015  |             |
| KR |    20150087727 A  | * | 7/2015  | ........... C12N 5/0696 |
| KR | 10-2016-0136224 A |   | 11/2016 |             |
| KR | 10-2017-0098938 A |   | 8/2017  |             |
| KR |    20170098938 A  | * | 8/2017  | ............. A61P 37/04 |
| WO | WO 2016/109661 A1 |   | 7/2016  |             |
| WO | WO 2017/070337 A1 |   | 4/2017  |             |
| WO | WO 2017/078807 A1 |   | 5/2017  |             |

OTHER PUBLICATIONS

Cichocki, F. et al, "GSK3 inhibition drives maturation of NK cells and enhances their antitumor activity".Cancer Research. Aug. 8, 2017, 77(20), 5664-5675. (Year: 2017).*
English translation of KR-20150087727-A (Year: 2022).*
English translation of KR-20170098938-A (Year: 2022).*
Zhao et al., "CH223191 Is a Ligand-Selective Antagonist of the Ah (Dioxin) Receptor". Toxicological Sciences. Jul. 15, 2010. 117(2), 393-403 (Year: 2010).*
Boitano et al. "Aryl Hydrocarbon Receptor Antagonists Promote the Expansion of Human Hematopoietic Stem Cells". Science. Sep. 10, 2010. 329, 1345-1348 (Year: 2010).*
D'Souza, Saritha S., et al., "GSK3β Inhibition Promotes Efficient Myeloid and Lymphoid Hematopoiesis from Non-human Primate-Induced Pluripotent Stem Cells," *Stem cell reports*, 6, 2, 2016 (pp. 243-256).
Extended European Search Report issued on May 11, 2021 in counterpart European Patent Application No. 18858679.6 (10 pages in English).
International Search Report issued on Apr. 9, 2019 in corresponding International Patent Application No. PCT/KR2018/011247 (2 pages in English, 2 pages in Korean).
Cichocki et al., "GSK3 Inhibition Drives Maturation of NK Cells and Enhances Their Antitumor Activity," Cancer Research, Aug. 8, 2017, vol. 77, No. 20, pp. 5664-5675.

(Continued)

*Primary Examiner* — Allison M Fox
*Assistant Examiner* — Hanan Isam Abuzeineh
(74) *Attorney, Agent, or Firm* — NSIP Law

(57) ABSTRACT

The present invention relates to a method for producing natural killer cells using direct reprogramming, natural killer cells produced thereby, a biomarker specific to the natural killer cells, a cell therapeutic agent comprising the natural killer cells, a composition for treatment and prevention of cancer, a cryopreservation cell vial for storing the natural killer cells, and a medium kit for inducing the direct reprogramming. Exhibiting excellent proliferative potential and cancer cell killing potential, the natural killer cells produced by the production method can be effectively utilized for mass production and in a composition for treatment and prevention of cancer.

11 Claims, 21 Drawing Sheets

(56) References Cited

OTHER PUBLICATIONS

Eguizabal et al., "Natural killer cells for cancer immunotherapy: pluripotent stem cells-derived NK cells as an immunotherapeutic perspective," Frontiers in Immunology, 2014, 5:Article 439, 10 pages.

Galat et al., "Cytokine-free directed differentiation of human pluripotent stem cells efficiently produces hemogenic endothelium with lymphoid potential," Stem cell Research & therapy, Mar. 2017, 8:67, 11 pages.

Hughes et al., "AHR prevents human IL-1R1hi ILC3 differentiation to natural killer cells," NIH Public Access, Cell Rep, 2014, 8(1):150-162, 25 pages.

Koehl et al., "Clinical grade purification and expansion of NK cell products for an optimized manufacturing protocol," Frontiers in Oncology, May 17, 2013, 3:Article 118, 12 pages.

Yoon et al., "Understanding of molecular mechanisms in natural killer cell therapy," Experimental & Molecular Medicine, 2015, 47, e141, 11 pages.

Rosenberg et al., "The Development of New Immunotherapies for the Treatment of Cancer Using Interleukin-2," Annals of Surgery, Aug. 1988, vol. 208, No. 2, pp. 121-135.

\* cited by examiner

METHOD FOR PRODUCING NATURAL KILLER CELL AND USE THEREOF

CROSS REFERENCE TO RELATED APPLICATION(S)

This application is a U.S. national stage application of International Application No. PCT/KR2018/011247 filed on Sep. 21, 2018, which claims the benefit of Korean Patent Application Nos. 10-2017-0121980 filed on Sep. 21, 2017 and 10-2018-0113308 filed on Sep. 20, 2018, in the Korean Intellectual Property Office, the entire disclosures of which are incorporated herein by reference for all purposes.

TECHNICAL FIELD

The present invention relates to a method for producing natural killer cells using direct reprogramming and uses thereof.

BACKGROUND ART

Natural killer cells, which are important cells responsible for innate immunity, are cells that have the ability to recognize cancer cell-specific antigens to suppress the proliferation or metastasis of cancer cells. Natural killer cells have contact-dependent cytotoxicity and play an important role in removing abnormal cells by producing cytokines associated with immune regulation. Target tumor cell death (apoptosis) is mediated by selectively killing tumor cells by secretion of cytokines such as perforin (Prf1), granzyme B (GzmB), interferon-γ, and tumor necrosis factor-α (TNF-α) (Yoon S R, et al. (2015), *Exp Mol Med* 47:e141). Due to the nature of these natural killer cells, natural killer cells are useful resources for overcoming the limitations of existing anti-cancer treatment methods, such as anti-cancer therapeutic agents, cancer recurrence inhibitors, etc., and technology development to maximize their use has been actively conducted.

A previous study has shown that when lymphocytes in the resting period are cultured in vitro with IL-2, lymphokine-activated killer cells capable of killing tumor cells can be achieved, and when co-cultured with melanoma, kidney cancer, and colon cancer cells using the same, it was found that lymphocytes have anti-cancer effects by confirming that about 30% of cancer cells were killed (Rosenberg (1988), *A review. Ann Surg* 208 (2): 121-135). However, lymphokine-activated killer cells are difficult to mass cultivate, and side effects accompanied by capillary leak syndrome such as hypotension and dyspnea due to high concentration of IL-2 added to sustain the killing effect have emerged as a problem.

In the past decades, the development and utilization fields of immunotherapeutics using natural killer cells have been rapidly growing, and the quantitative needs for technology demand are rapidly increasing, and thus the mass production technology of allogeneic and autologous human natural killer cells is highlighted as a key technology in the development of immunotherapeutics. As a source of human natural killer cell resources, the method of isolating and proliferating natural killer cells from peripheral blood is mainly used, and technology for producing natural killer cells through differentiation-inducing culture from stem cells such as human hematopoietic stem cells, embryonic stem cells, and induced pluripotent stem cells, which have excellent differentiation ability, is also actively developed multidimensionally. However, it has been pointed out as a problem that it takes a long period of time to induce differentiation of natural killer cells from stem cells with high cost, low efficiency, etc. Recently, besides the technique of producing target cells through differentiation-induced culture using the differentiation potential of stem cells, a technique for directly producing high value-added human tissue-specific target cells having different lineage characteristics from early human somatic cells that are relatively easy to secure using somatic reprogramming technology is rapidly being developed. This has emerged as a new alternative that can overcome the problems of the prior art for securing human somatic cells, suggesting endless application possibilities such as academic or clinical application, the utilization of new drug development, etc., and technology development is in progress for a variety of cell types. However, there has been no report so far on the achievement of technology development for directly producing natural killer cells via direct reprogramming as in the present invention.

DISCLOSURE

Technical Problem

As a result of tremendous efforts to develop a method for producing human natural killer cells with high efficiency, the present inventors completed the present invention by confirming that through direct reprogramming-inducing culture from isolated human somatic cells, natural killer cells can be produced in a relatively fast time with high efficiency, and the produced natural killer cells have an effect as an immune cell therapeutic agent for anti-cancer drugs.

Technical Solution

An object of the present invention is to provide a method for producing natural killer cells, comprising (a) introducing a reprogramming factor into isolated cells; and (b) culturing the cells of step (a) in i) a first medium comprising cytokine, growth factor, and GSK3β inhibitor, and ii) a second medium comprising cytokine and growth factor to directly reprogram into natural killer cells.

Another object of the present invention is to provide natural killer cells produced according to the above method.

Still another object of the present invention is to provide a cell therapeutic agent, comprising the natural killer cells produced according to the above method.

Still another object of the present invention is to provide a pharmaceutical composition for treating or preventing cancer, comprising the natural killer cells produced according to the above method as an active ingredient.

Still another object of the present invention is to provide a method for preparing a cell vial for cryopreservation, comprising (a) introducing a reprogramming factor into isolated cells; and (b) culturing the cells of step (a) in i) a first medium comprising cytokine, growth factor, and GSK3β inhibitor, and ii) a second medium comprising cytokine and growth factor to directly reprogram into natural killer cells.

Still another object of the present invention is to provide a cell vial for cryopreservation prepared according to the above method.

Still another object of the present invention is to provide a medium kit for inducing direct reprogramming, comprising a first container comprising a first medium of cytokine, growth factor, GSK3β inhibitor, StemRegenin I, interleukin 7, and interleukin 15; and a second container comprising a second medium of cytokine, growth factor, StemRegenin I, and CH-223191.

Advantageous Effect

Compared to methods of obtaining natural killer cells through the existing stem cell differentiation process, the method for producing natural killer cells using the direct reprogramming of the present invention has a significantly low initial (patient) cell usage, enables the securing of a large amount of natural killer cells within a short time, and has excellent cancer cell killing potential of secured natural killer cells. Thus, it can be effectively utilized for mass production of natural killer cells, and the cell therapeutic agent and pharmaceutical composition comprising the natural killer cells can be used for treatment or prevention of cancer.

In addition, biomarkers specific to natural killer cells produced by the above production method were selected in the present invention, and through this, it was confirmed that genes that were up-regulated with hematopoietic cell lineage and natural killer cell-mediated cytotoxicity factors associated with cell differentiation and anti-cancer mechanisms were identified. Also, as these were confirmed to retain their characteristics upon thawing after cryopreservation, the natural killer cells can be effectively utilized as a composition for treating or preventing cancer.

BRIEF DESCRIPTION OF DRAWINGS

A of FIG. 1 is a diagram briefly describing a method for producing natural killer cells by direct reprogramming, and B is a diagram showing the production of natural killer cells depending on whether four reprogramming factors are introduced.

Figure 4:
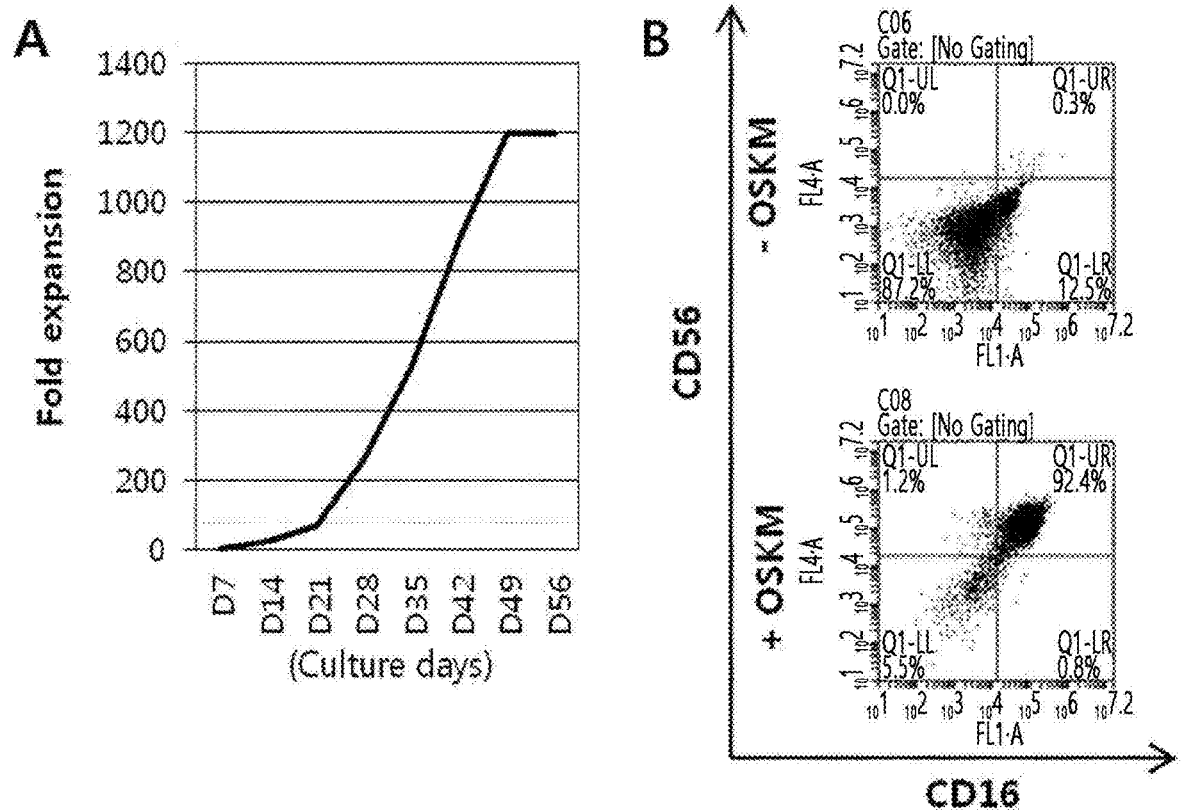

A of FIG. 4 is a diagram showing the proliferation potential of reprogramming-induced natural killer cells, and B is a diagram showing the production of natural killer cells depending on whether reprogramming factors are introduced.

Figure 5:
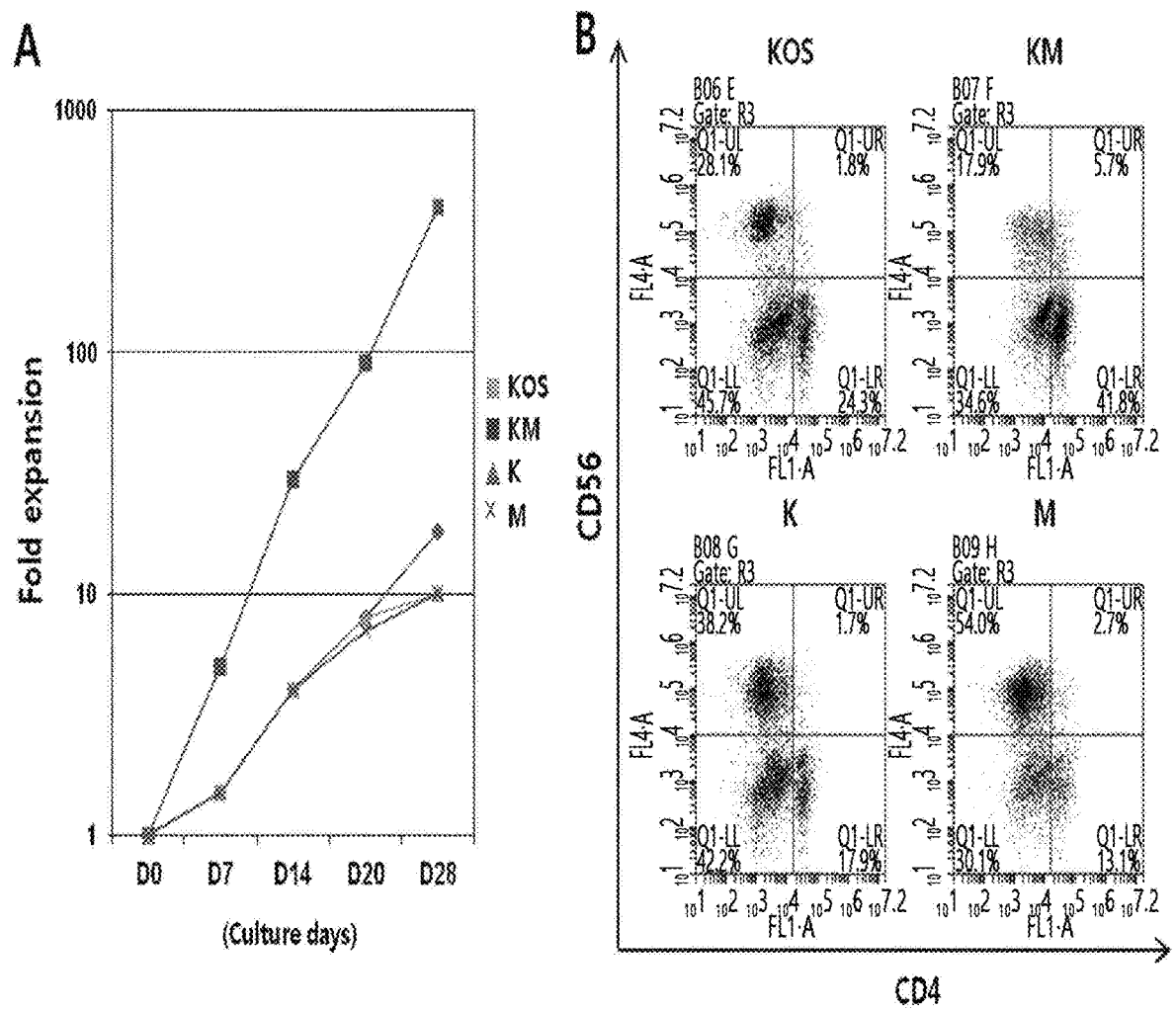

A of FIG. 5 is a diagram showing cell proliferation potential depending on reprogramming factors, and B is a diagram showing the production of natural killer cells depending on reprogramming factors.

Figure 6:
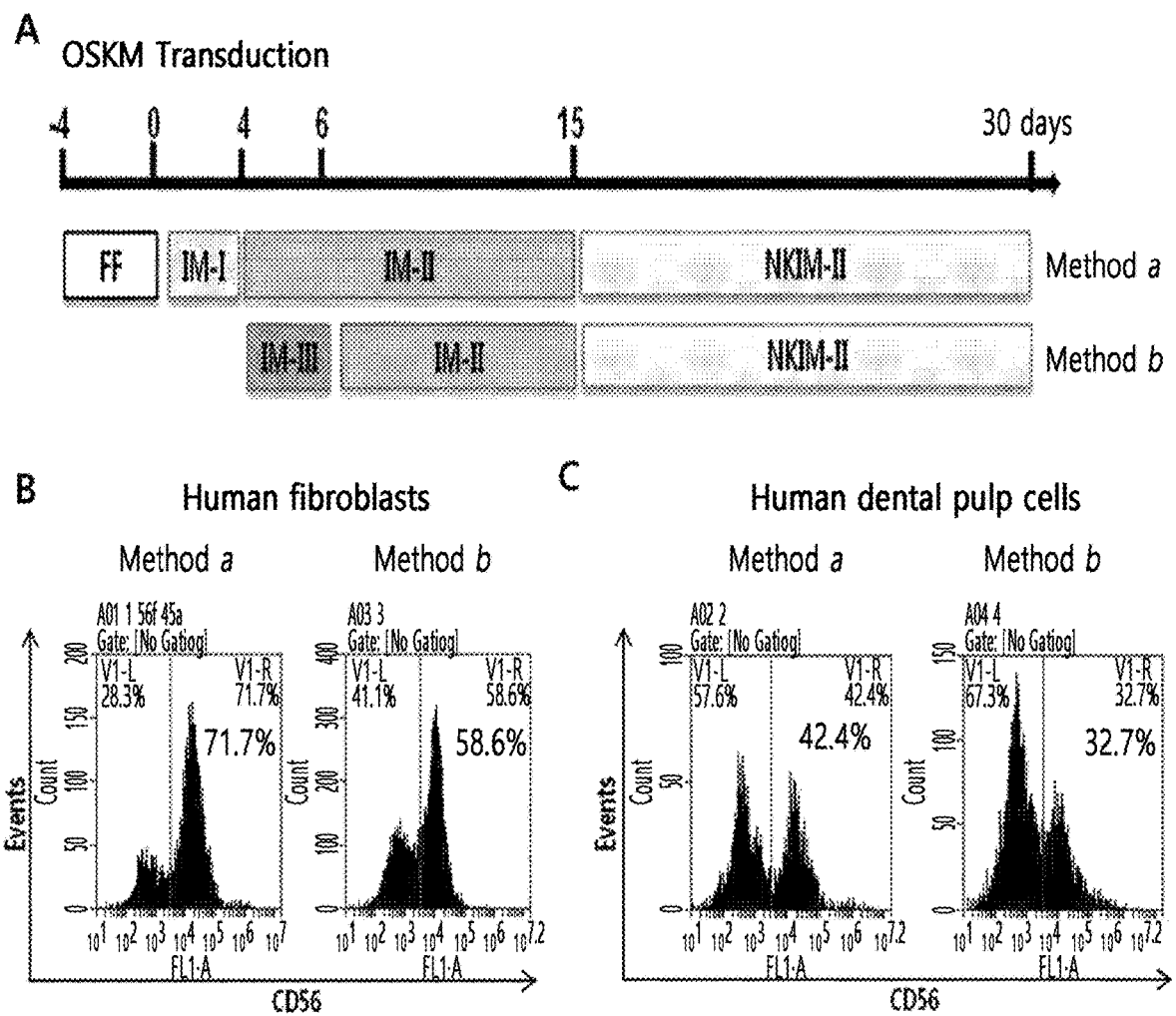

A of FIG. 6 is a diagram briefly describing the methods a and b of producing natural killer cells, and B and C are diagrams showing the production of natural killer cells by the methods a and b in human skin fibroblasts and human dental pulp cells, respectively.

Figure 7:
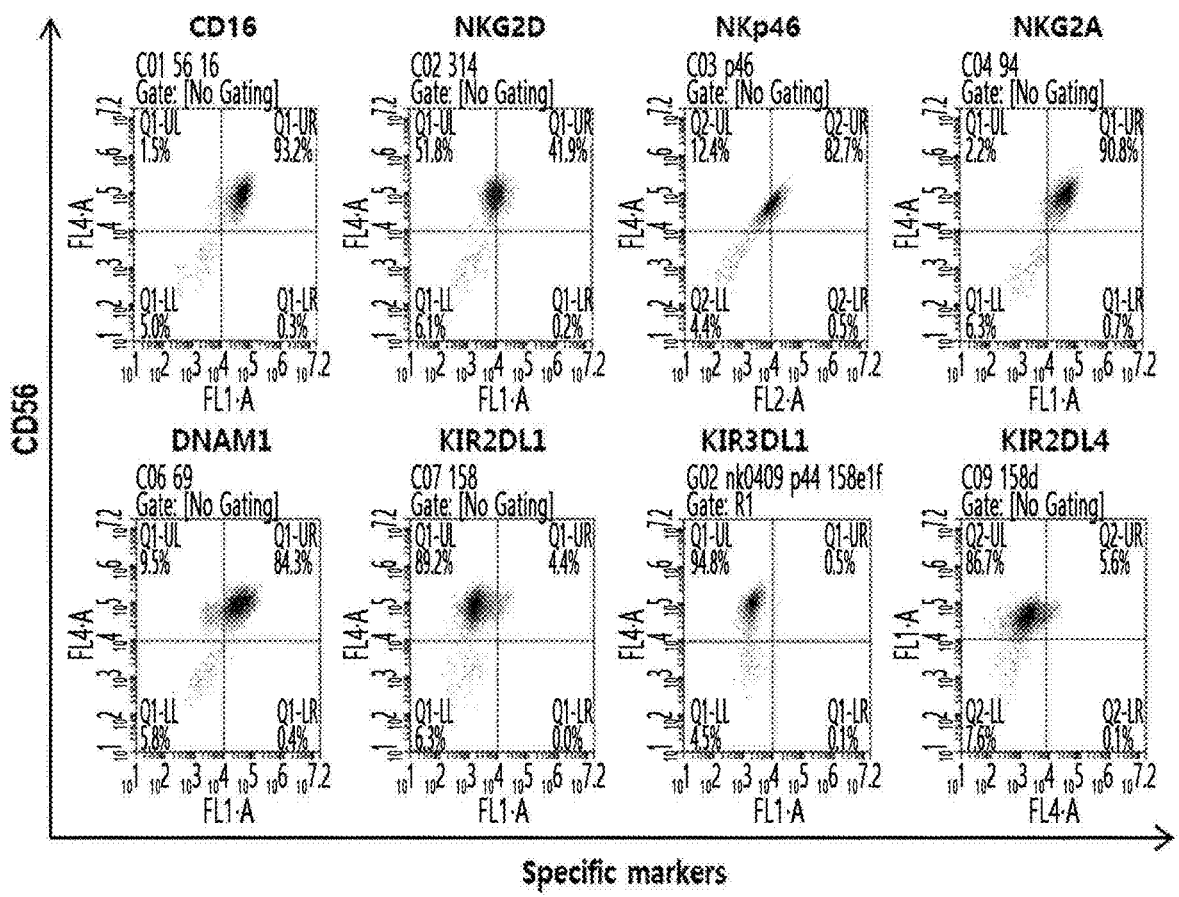

FIG. 7 is a diagram showing a marker expression pattern of reprogramming-induced natural killer cells.

Figure 8:
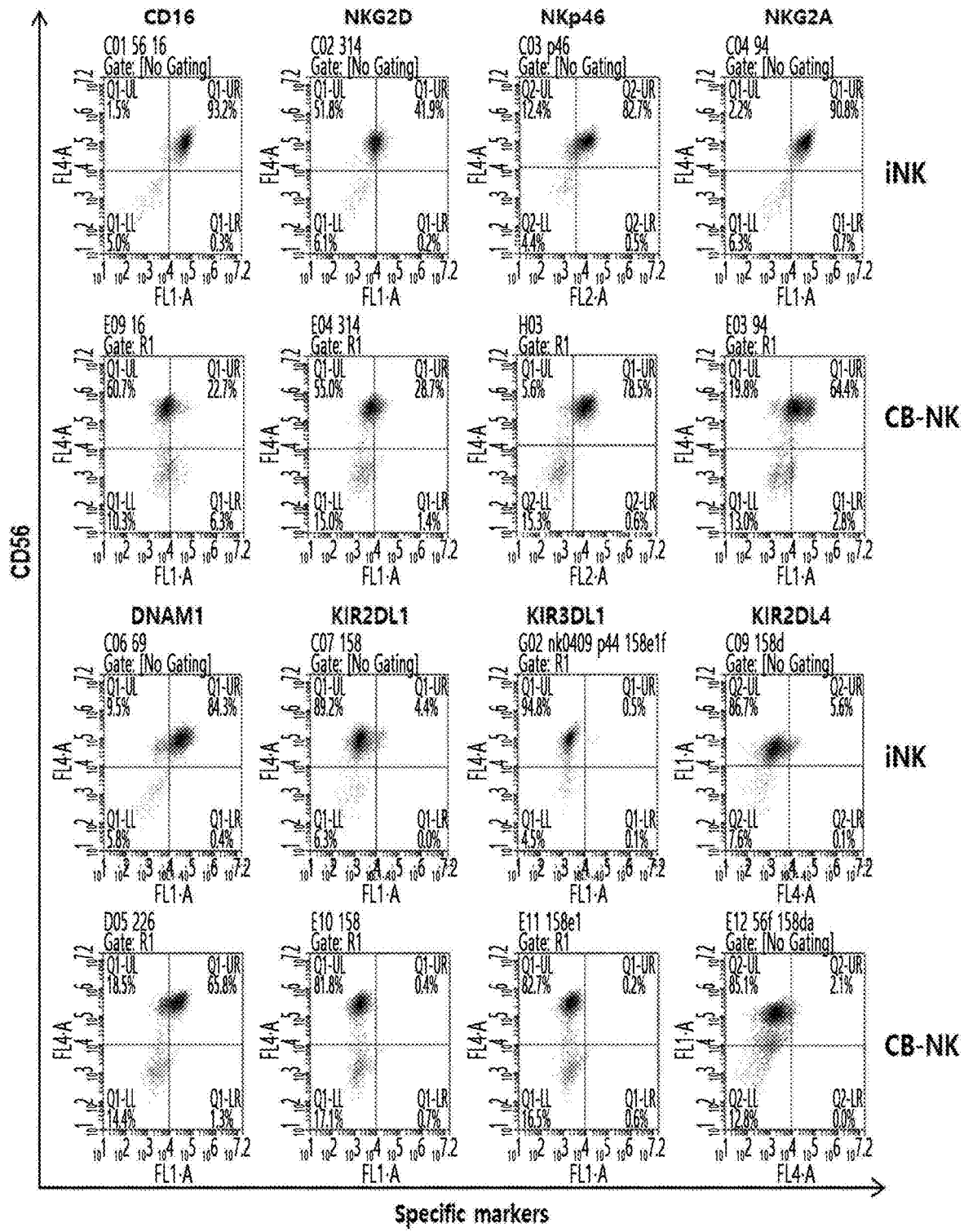

FIG. 8 is a diagram showing the results of comparative experiments comparing the marker expression patterns of reprogramming-induced natural killer cells (iNK) and umbilical cord blood cell-derived natural killer cells (CB-NK).

Figure 9A:
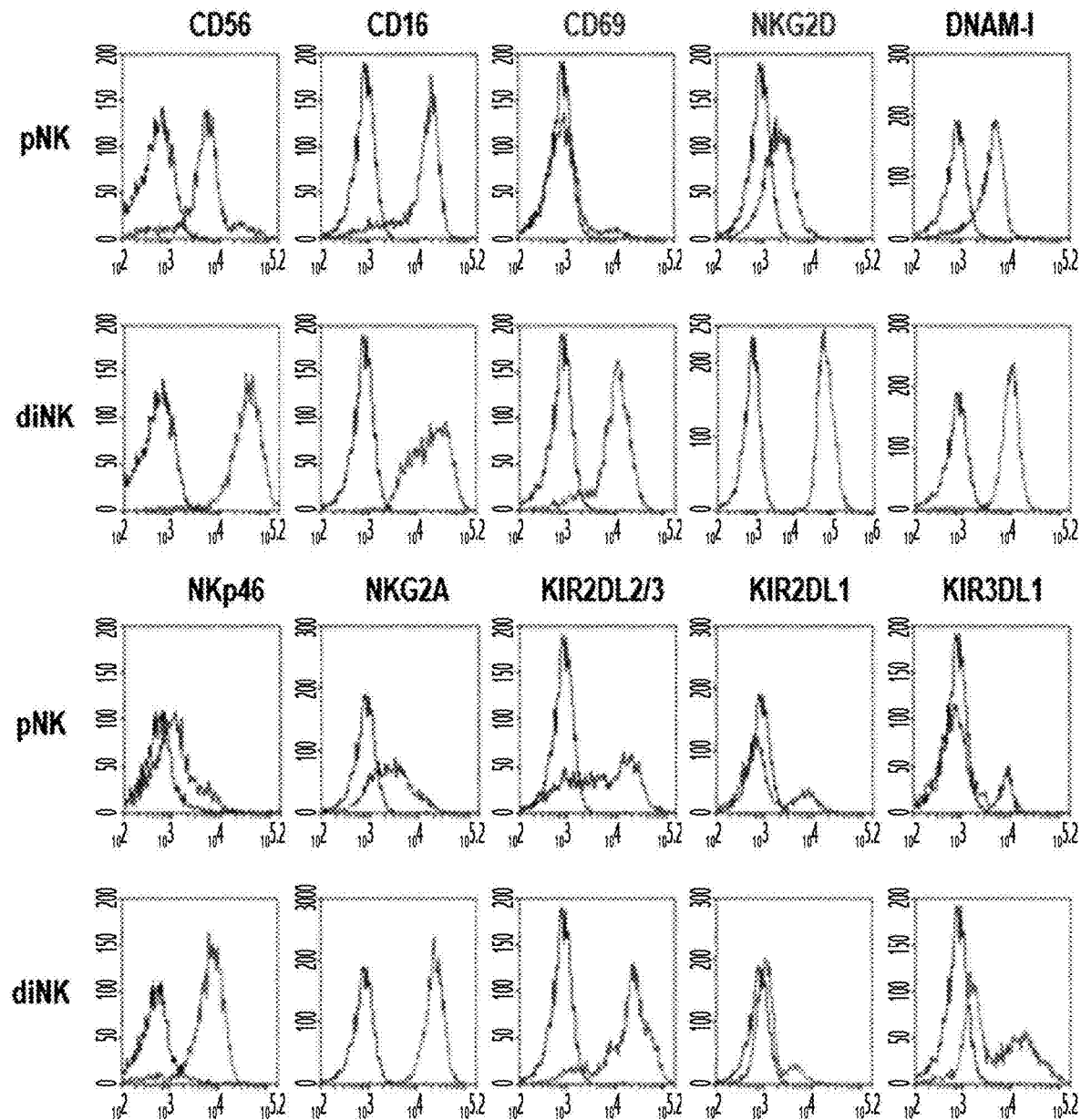
Figure 9B:
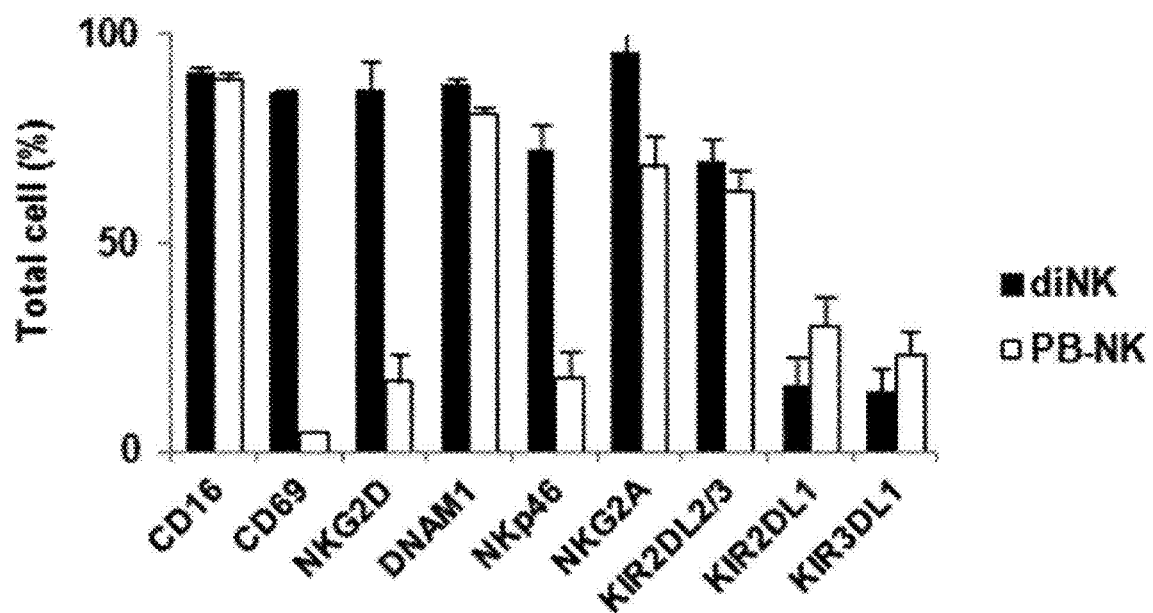
Figure 9C:
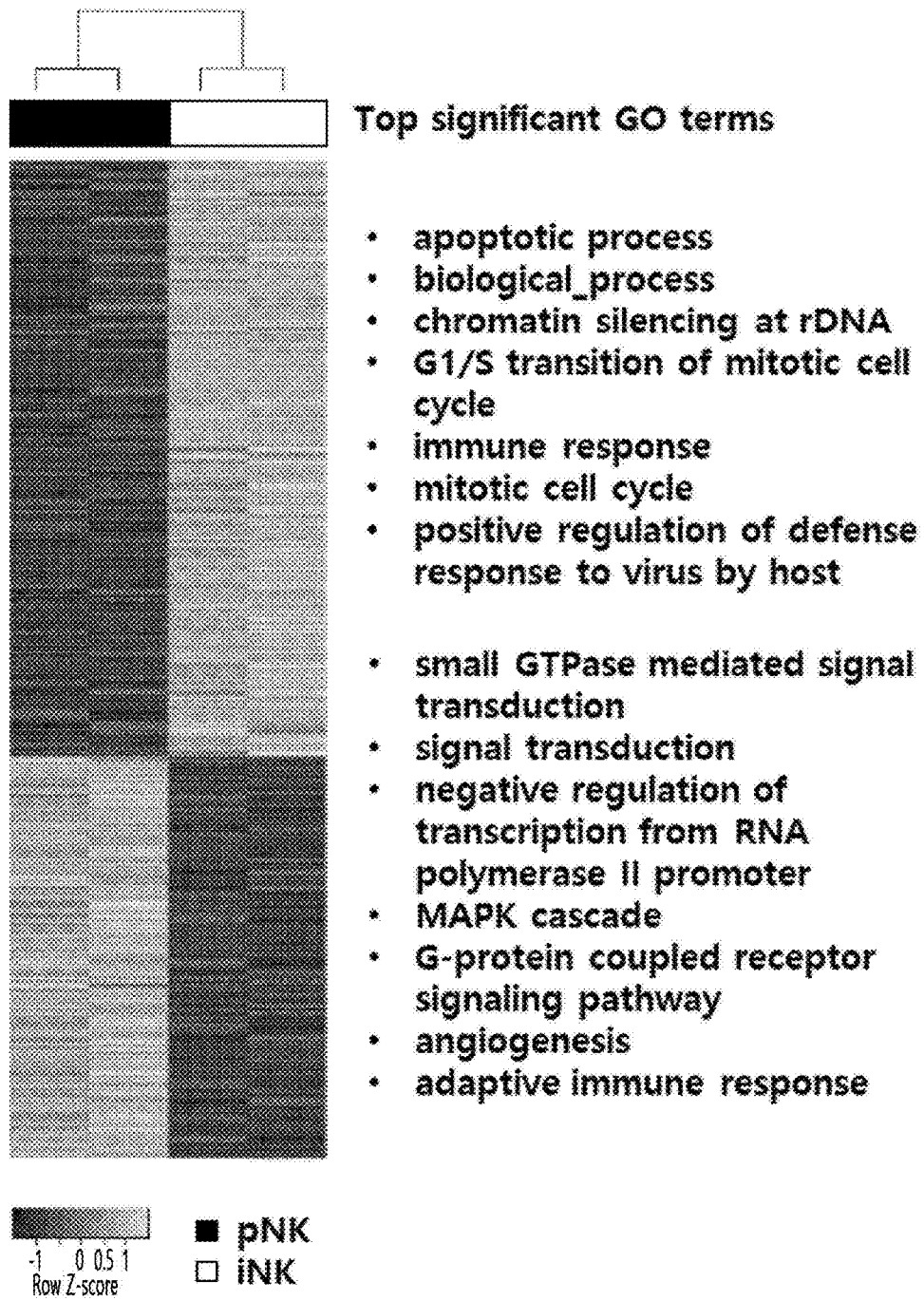

FIG. 9A is a diagram showing flow cytometry analysis of the expression characteristics of the cell surface receptors of peripheral blood natural killer cells and induced natural killer cells, FIG. 9B is a diagram showing the comparison of the activation level of the two cells, and FIG. 9C is a diagram showing microarray analysis confirming genes that were up- or down-regulated in induced natural killer cells.

Figure 10:
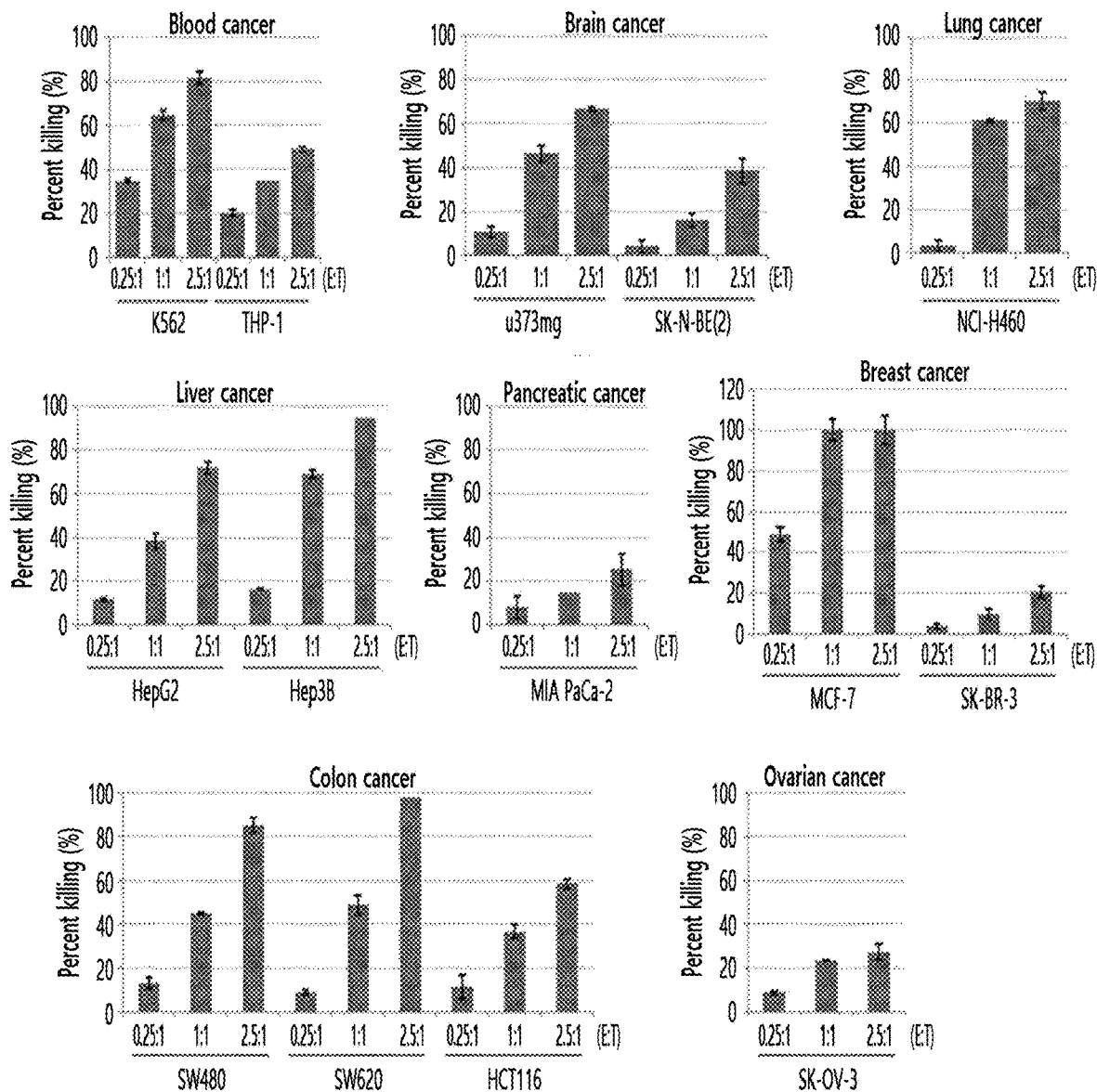

FIG. 10 is a diagram showing the cancer cell killing potential of natural killer cells against blood cancer, brain cancer, lung cancer, liver cancer, pancreatic cancer, breast cancer, colon cancer, and ovarian cancer cell lines.

Figure 11:
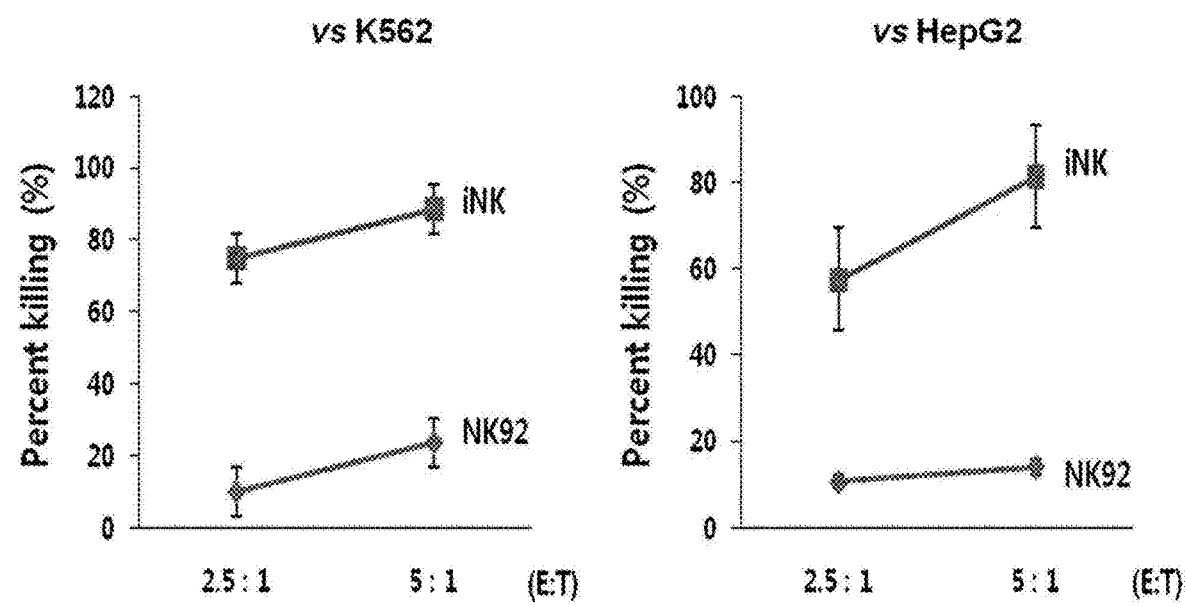

FIG. 11 is a diagram showing the results of comparative experiments for the cancer cell killing potentials of reprogramming-induced natural killer cells (iNK) and existing natural killer cells (NK92).

Figure 12A:
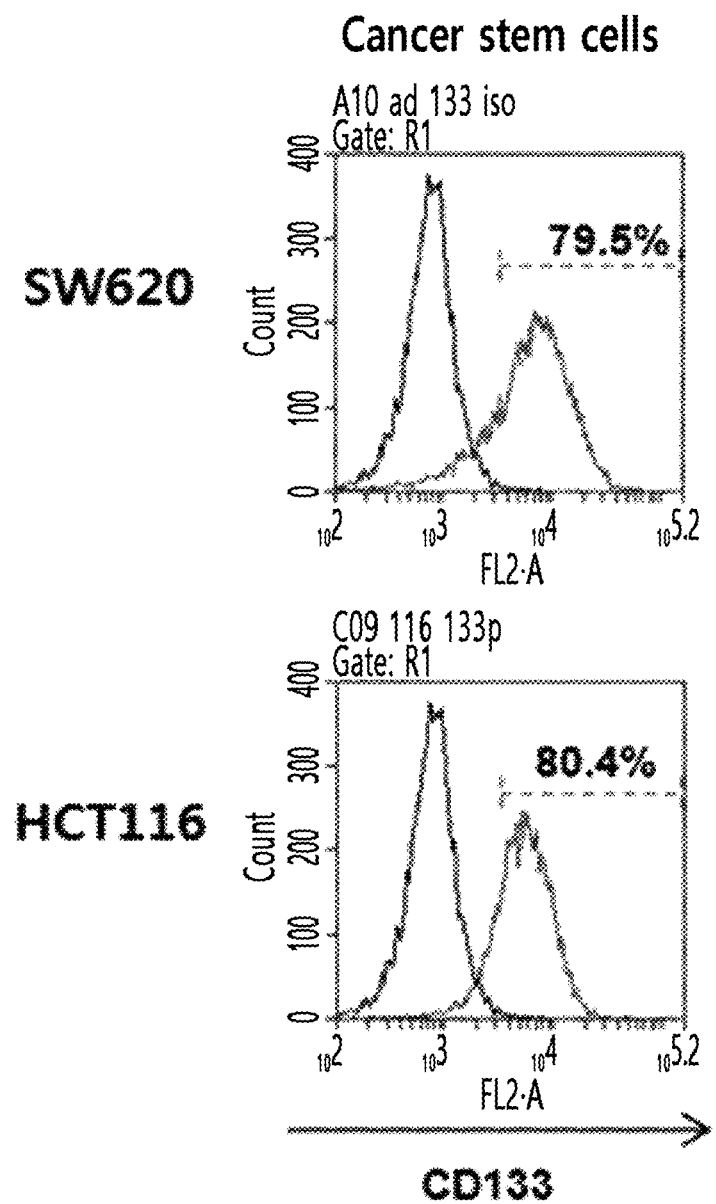
Figure 12B:
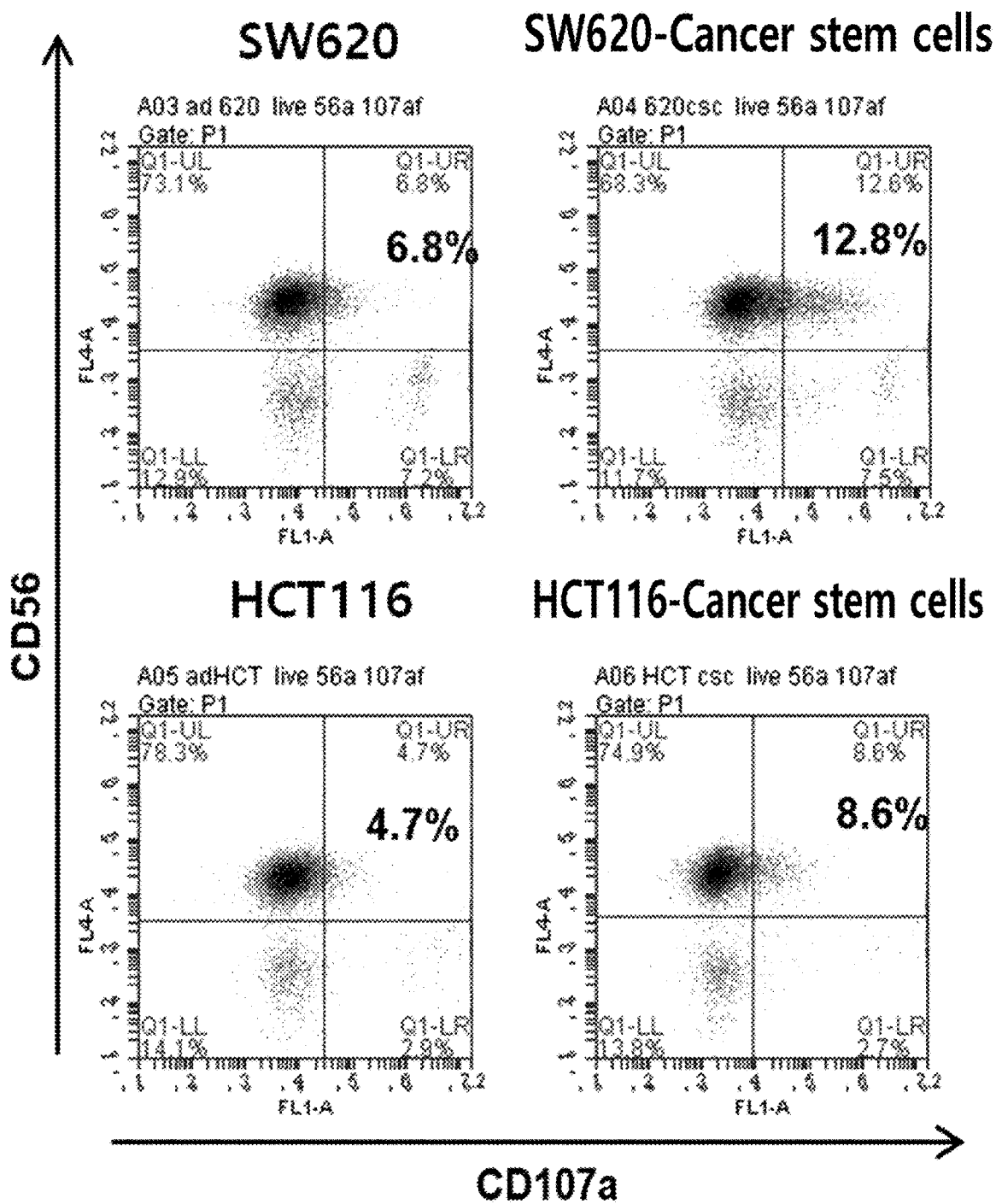

FIG. 12A is a diagram showing the yield of cancer stem cells of SW620 and HCT116, which are colon cancer cells, and FIG. 12B is a diagram showing a comparison of the killing potentials of induced natural killer cells against the cancer cells and cancer stem cells.

Figure 13A:
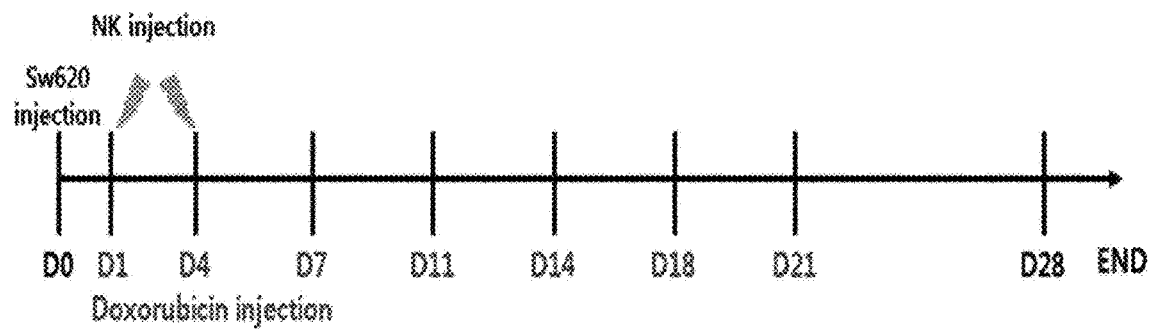
Figure 13B:
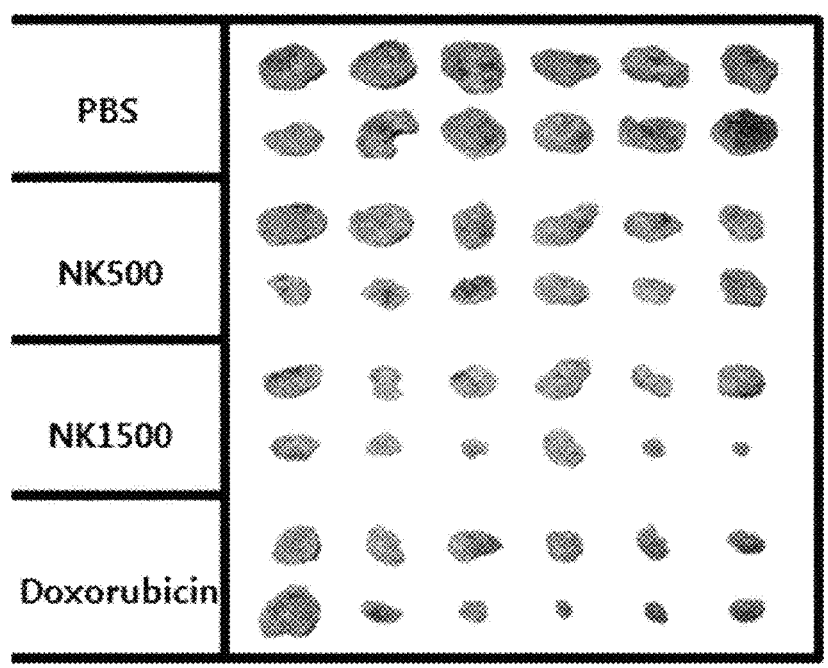
Figure 13C:
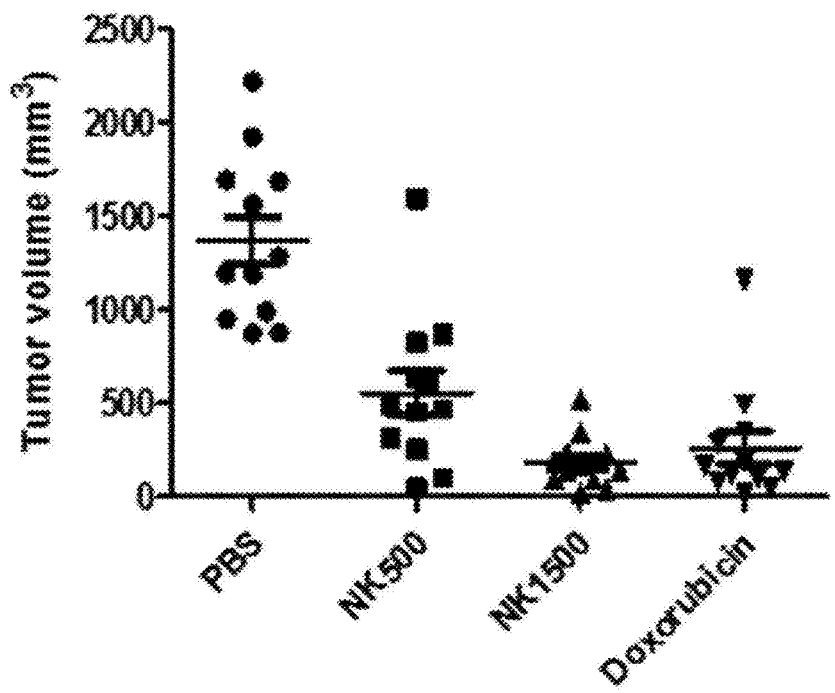

FIG. 13A is a diagram showing the experiment performance date for confirming the anti-cancer effect in vivo of induced natural killer cells, and FIG. 13B and FIG. 13C are diagrams showing the changes in tumor size confirming the anti-cancer effect of induced natural killer cells.

Figure 14:
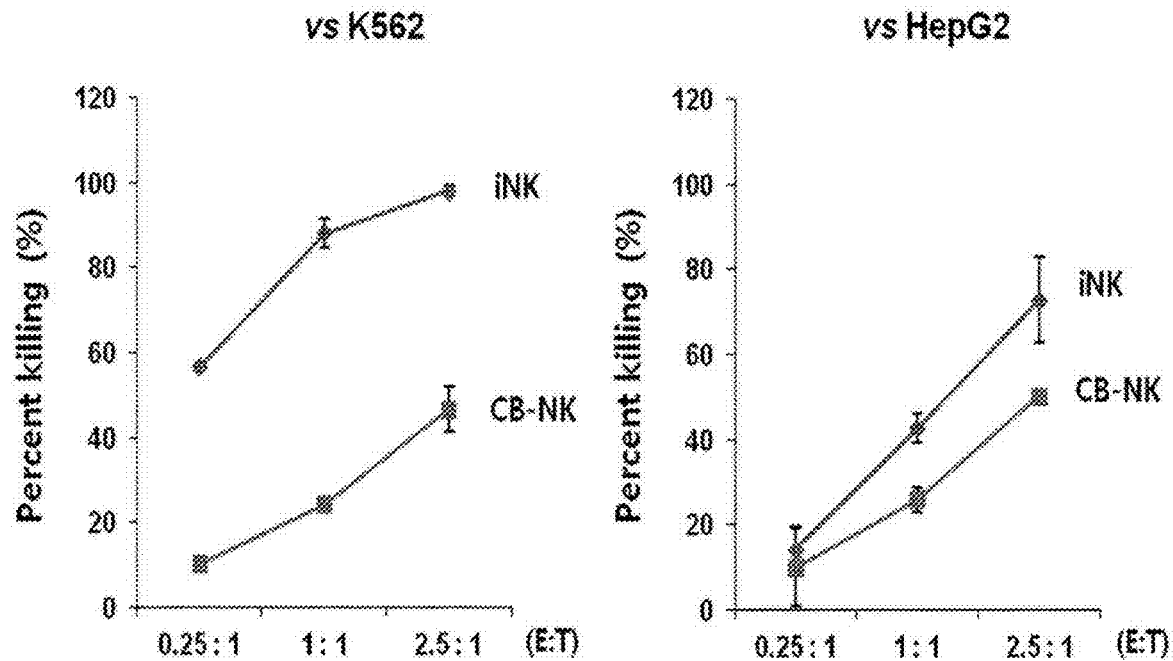

FIG. 14 is a diagram showing comparative experiments of the cancer cell killing potential of reprogramming-induced natural killer cells (iNK) and umbilical cord cell-induced natural killer cells (CB-NK).

Figure 15:
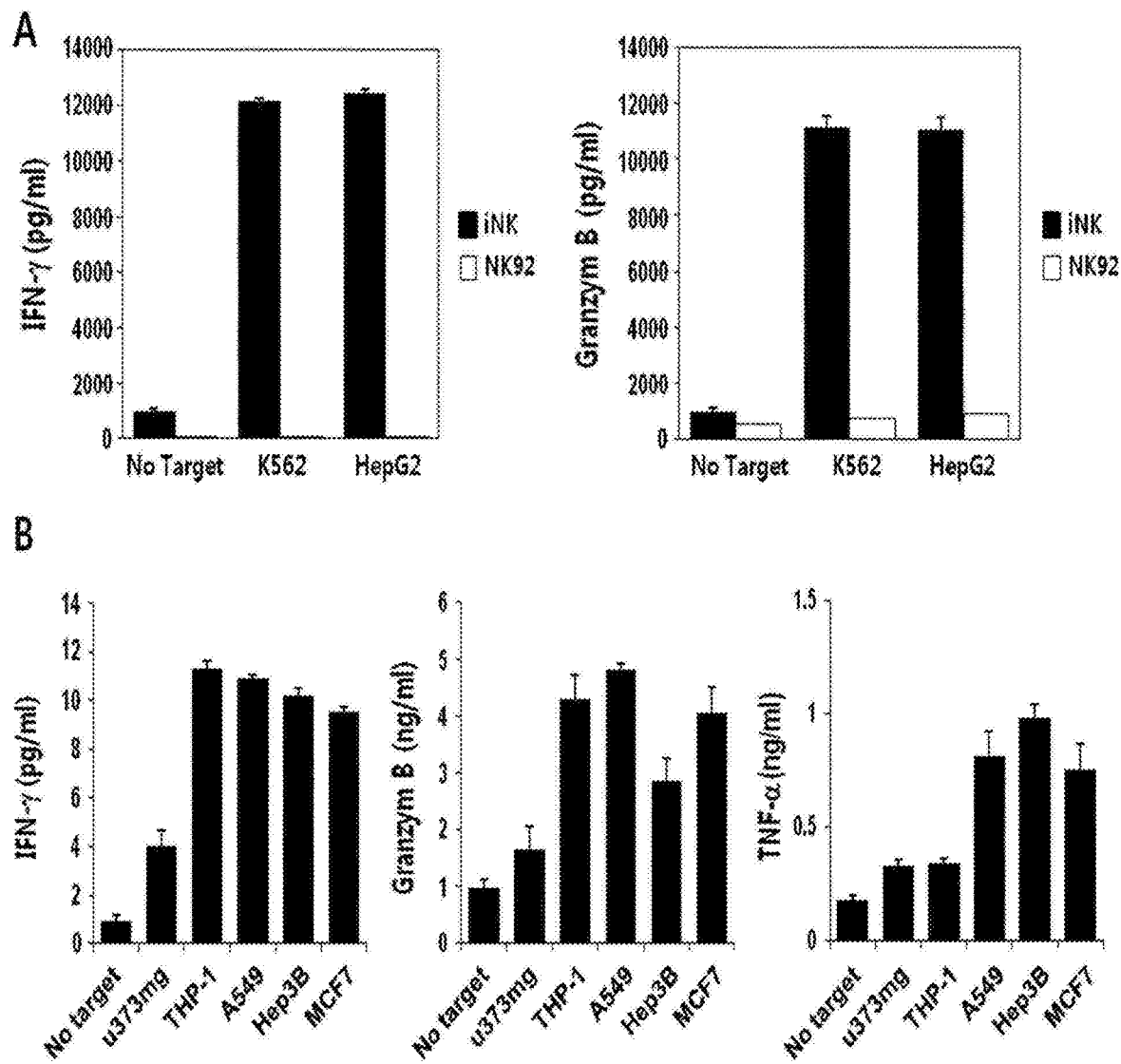

A of FIG. 15 is a diagram showing the results of comparative experiments of the secretion potentials of cytokine INF-γ and granzyme B when co-culturing existing natural killer cells and mentioned cancer cells. B is a diagram showing the secretion potentials of cytokine INF-γ, granzyme B, and TNF-α when co-culturing with the mentioned cancer cells.

Figure 16:
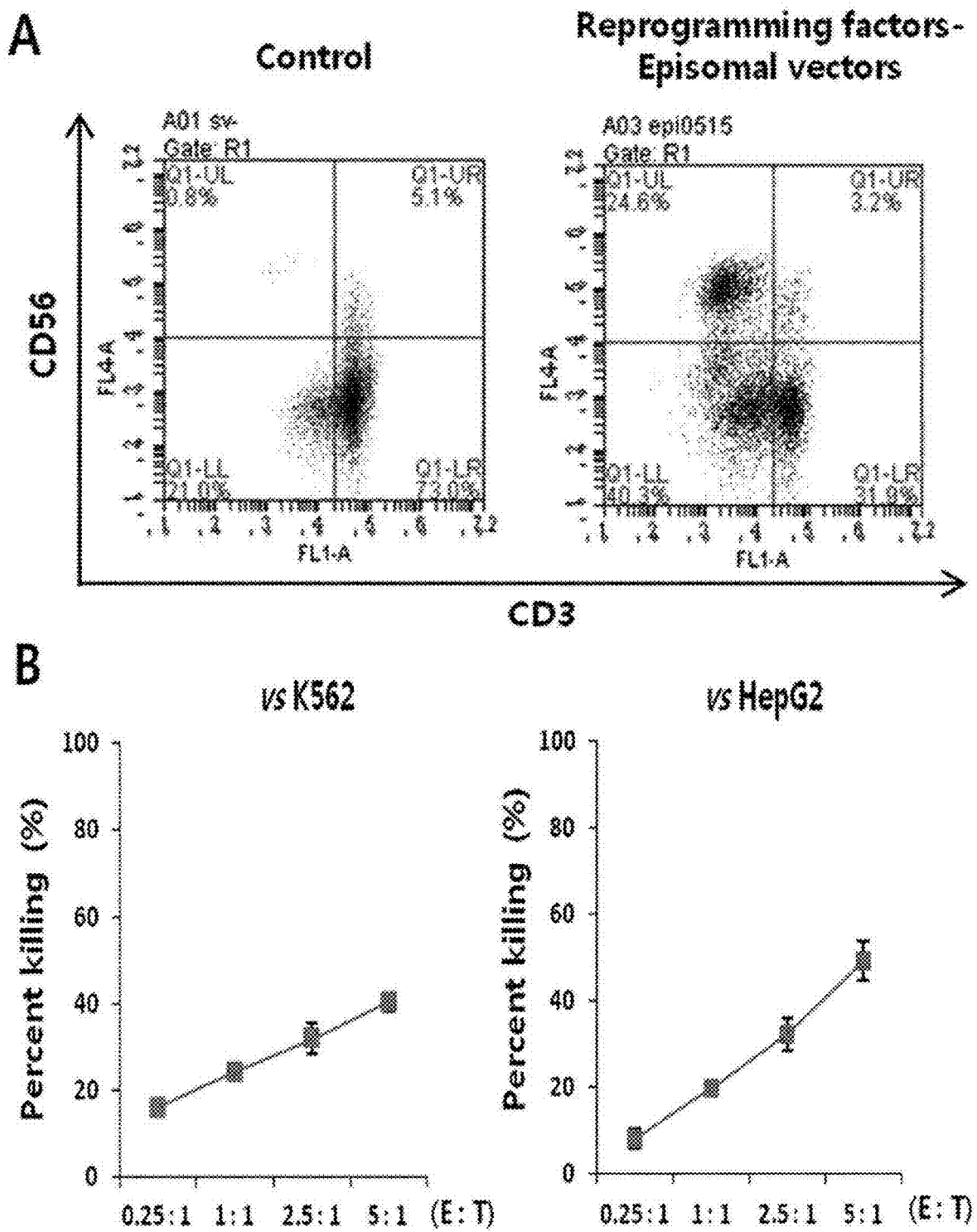

A of FIG. 16 is a diagram showing the production of natural killer cells directly reprogrammed using non-integrative episomal vectors. B is a diagram showing the cancer cell killing potential of the natural killer cells.

Figure 17:
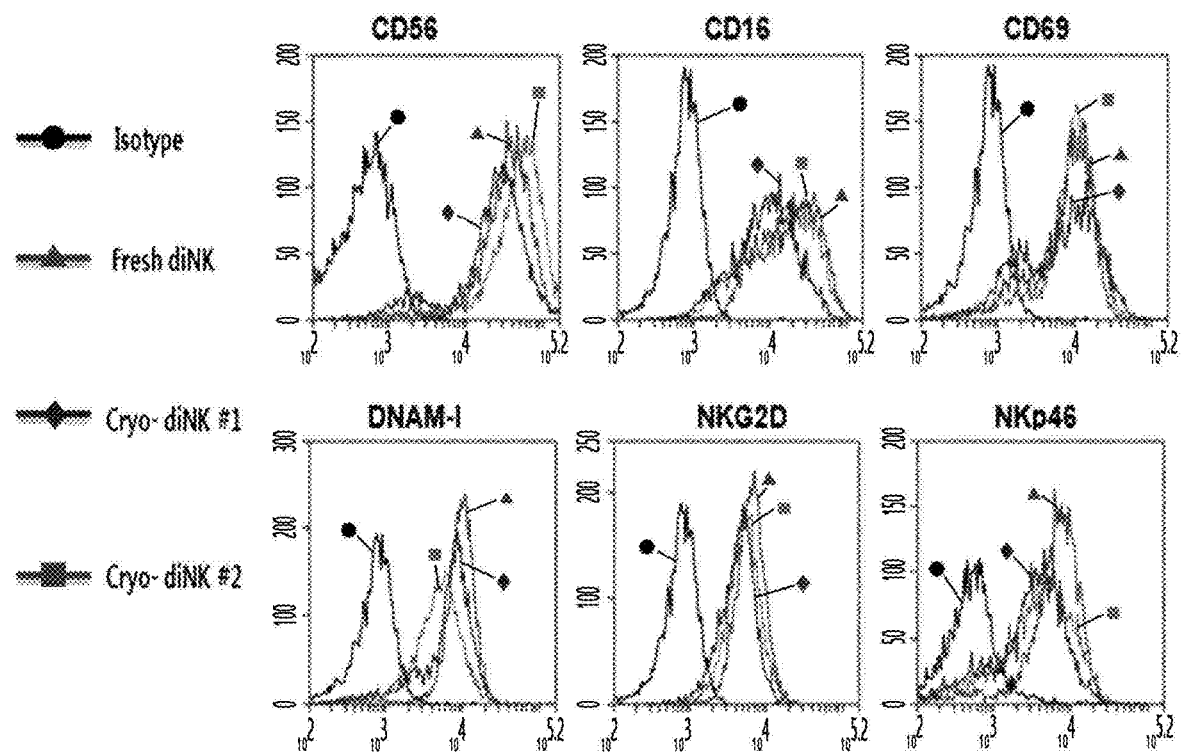

FIG. 17 is a diagram showing the characteristics of cryopreserved induced natural killer cells.

BEST MODE

Each description and embodiment disclosed in the present application may be applied to each other description and embodiment. That is, all combinations of the various elements disclosed in the present application are within the scope of the present application. In addition, it cannot be deemed that the scope of the present application is limited by the specific descriptions described below.

As one aspect for achieving the objects of the present invention, the present invention provides a method for producing natural killer cells, comprising (a) introducing a reprogramming factor into isolated cells; and (b) culturing the cells of step (a) in i) a first medium comprising cytokine, growth factor, and GSK3β inhibitor, and ii) a second medium comprising cytokine and growth factor to directly reprogram into natural killer cells.

In the present invention, step (a) is a step of (i) introducing one or more reprogramming factors into isolated cells.

As used herein, the term "isolated cell", while not particularly limited, may specifically refer to cells in which lineage is already specified, such as germ cells, somatic cells, or progenitor cells. For example, they may be cells derived from humans, but cells derived from various subjects are also within the scope of the present invention.

In addition, the isolated cells of the present invention may include both in vivo or ex vivo cells, and specifically, they may be cells isolated from the living body.

The term "somatic cell" refers to all cells that have completed differentiation constituting animals and plants, except for germ cells, and the "progenitor cell" refers to a parent cell that does not express a differentiation trait, but has a differentiation fate, when the cell corresponding to the progeny is found to express a specific differentiation trait. For example, for nerve cells (neurons), neuroblasts (neuron stem cells) correspond to progenitor cells, and for root canal cells, myocytes correspond to progenitor cells.

In a specific embodiment of the present invention, it was confirmed that natural killer cells were produced by direct reprogramming of peripheral blood mononuclear cells (Example 1), and fibroblasts, and dental pulp cells (Example 6).

As used herein, the term "reprogramming factor" refers to a gene (or polynucleotide encoding it) or protein that can be introduced into a cell and induce reprogramming. The reprogramming factor may vary depending on the target cell to induce reprogramming and the type of isolated cells in which reprogramming is induced. For example, in the case of producing natural killer cells, the reprogramming factor may comprise one or more factors selected from the group consisting of Lin28, Asc11, Pitx3, Nurr1, Lmx1a, Nanog, Oct3, Oct4, Sox2, Klf4, and Myc, and other than theses, it may comprise all factors known in the art that can produce natural killer cells. In addition, direct reprogramming into natural killer cells can be induced using the reprogramming factor. There is a method of using a reprogramming genetic factor in the direct reprogramming methodology, and the vector of the present invention can be utilized for such use. Therefore, those skilled in the art can select a suitable factor depending on the type of the target cell and the cell before being reprogrammed, all of which is included within the scope of the present invention, as long as it is within the scope known in the art, and the type thereof is not particularly limited. Reprogramming using the reprogramming genetic factor controls the overall gene expression pattern that cells have, thereby inducing the conversion to the target cell, and thus the reprogramming genetic factor is introduced into a cell, and by culturing the cell for a period of time, the early cell can be reprogrammed to a target cell having a gene expression pattern of a desired type of cells.

In a specific embodiment of the present invention, direct reprogramming was induced by introducing a group of reprogramming factors comprising one or more genes selected from the group consisting of Oct4, Sox2, Klf4, and Myc into isolated cells. As a result, it was confirmed that natural killer cells were produced via direct reprogramming in cells into which Oct4, Sox2, Klf4, and Myc; Klf4, Oct4, and Sox2; Klf4 and Myc; Klf4; and Myc were introduced (Examples 1 to 5).

In the present invention, "a step of introducing a reprogramming factor" may refer to a method for increasing the expression levels of reprogramming factors in cells through reprogramming factors present in cells, in particular, a method of increasing the expression level of Oct4, Sox2, Klf4, and c-Myc gene; or an expression vector, genetic modification, introduction of a foreign expression gene, treatment of a substance having an expression inducing effect, etc., but it is not particularly limited as long as it increases the expression level of reprogramming factors. In particular, the step of introducing a reprogramming factor may be a method of inducing expression of a reprogramming factor under a desired time and condition.

Specifically, the method of introducing the reprogramming factor of step (a) into cells may be used without limitation in providing nucleic acid molecules (DNA or RNA) or proteins that are conventionally used in the art to cells. For example, a method of administering a reprogramming factor to a cell culture solution, a method of directly injecting a reprogramming factor into a cell, or a method of transforming a cell using an expression vector having a gene of a reprogramming factor may be used.

For the method of directly injecting the reprogramming factor into cells, any method known in the art may be selected and used, and while not particularly limited thereto, it may be applied by appropriately selecting among microinjection, electroporation, particular bombardment, direct muscle injection method, insulator, and a method using transposon.

As used herein, the term "expression vector" is a vector capable of expressing a target protein in a suitable host cell, and refers to a gene construct comprising essential regulatory elements operably linked to express a gene insert.

The expression vector of the present invention includes a signal sequence of a leader sequence for membrane targeting or secretion in addition to expression control elements such as a promoter, an operator, an initiation codon, a termination codon, a polyadenylation signal, and an enhancer, and can be variously prepared depending on the purpose. In addition, the expression vector includes a selectable marker for selecting a host cell containing the vector, and in the case of a replicable expression vector, it includes the origin of replication. Expression vectors can be self-replicating or integrated into host DNA.

The expression vector includes a viral vector, episomal vector, plasmid vector, cosmid vector, etc., but is not limited thereto.

Specifically, the viral vector may include vectors derived from lentivirus, retrovirus, for example, human immunodeficiency virus (HIV), murine leukemia virus (MLU), avian sarcoma/leucosis (ASLV), spleen necrosis virus (SNV), Rous sarcoma virus (RSV), mouse mammary tumor virus (MMTV), etc., adenovirus, adeno-associated virus, herpes simplex virus, etc. In addition, more specifically, it may be an RNA-based viral vector, but is not limited thereto.

In addition, the episomal vector of the present invention is a non-viral, non-integrative vector, and is known to have a property that it can express a gene included in the vector without being integrated into the chromosome. For the purpose of the present invention, cells comprising an episomal vector include all cases in which the episomal vector is integrated into the genome or is present in the cell without being integrated into the genome. In addition, the episomal vector may comprise one or more reprogramming factors.

As used herein, the term "operably linked" refers to a functional linkage between a nucleic acid expression control sequence and a nucleic acid sequence encoding a target protein to perform a general function. Operational linkage with recombinant vectors can be prepared using genetic recombination techniques well known in the art, and site-specific DNA cleavage and linkage use enzymes, etc. that are generally known in the art.

Next, step (b) is a step in which the cells of step (a) are cultured in i) a first medium comprising cytokine, growth factor, and GSK3β inhibitor, and ii) a second medium comprising cytokine and growth factor to directly reprogram into natural killer cells.

The first medium of step (b) may further comprise Stem-Regenin I, interleukin 7, interleukin 15, or a combination thereof, and the second medium of step (b) may further comprise StemRegenin I, CH-223191, or a combination thereof.

As used herein, the term "cytokine" is a variety of proteins of relatively small size that are produced in cells and used for cell signaling, and can affect other cells, including themselves. In general, it is associated with an immune response to inflammation or infection, but is not limited thereto. Specifically, the cytokine may be IL-2, IL-3, IL-5, IL-6, IL-7, IL-11, IL-15, BMP4, Acivin A, Notch ligand, G-CSF, and SDF-1, but is not limited thereto.

As used herein, the term "growth factor" refers to a polypeptide that promotes the division, growth, and differentiation of several cells, and includes epithelial cell growth factor (EGF), platelet-derived growth factor-AA (PDGF-AA), insulin-like growth factor-1 (IGF-1), transforming growth factor-β (TGF-β), or fibroblast growth factor (FGF), but is not limited thereto.

For the purpose of the present invention, cytokines and growth factor are included in a medium that directly reprograms isolated cells into lineage-converted cells, and is not limited to the types of cytokines and growth factor as long as they are used for direct reprogramming.

As used herein, the term "GSK3β inhibitor" is a substance that inhibits or suppresses the activity of GSK3β, which is one of the two isoform proteins of glycogen synthase kinase-3 (GSK3), and may include lithium, SB216763, CHIR-98014, TWS119, AR-A014418, etc., and may specifically be CT99021, but is not limited thereto.

In a specific embodiment of the present invention, it was confirmed that the natural killer cell production efficiency was more excellent when GSK3β inhibitor was comprised in the first medium of step (b) than the case where it was not comprised (Example 2). This suggests that GSK3β inhibitor plays an important role in the natural killer cell production method through direct reprogramming.

As used herein, the term "culture" refers to growing cells in appropriately controlled environmental conditions, and the culture process of the present invention can be made according to the appropriate medium and culture conditions known in the art. Such a culture process can be easily adjusted and used by those skilled in the art depending on the selected cell.

In particular, since step (B) is a process of culturing the cells in which the reprogramming factor is introduced in the first medium and the second medium, the composition of the first medium and the second medium for culturing the cells has a composition suitable for direct reprogramming of cells, into which the reprogramming factor is introduced, to natural killer cells. Specifically, the first medium may comprise cytokine, growth factor, and GSK3β inhibitor, and the second medium may comprise cytokine and growth factor, but these media are not limited thereto.

As used herein, the term "medium" refers to a known medium that is used for culturing cells, and is meant to include all known media for cell culture or modified media thereof.

The term "StemRegenin I" of the first medium is an aryl hydrocarbon receptor inhibitor and refers to (4-(2-((2-benzo[b]thiphen-3-yl)-9-isopropyl-9H-purin-6-yl)amino)ethyl) phenol hydrochloride. In addition to the cytokine, growth factor, and GSK3 β inhibitor of the first medium, the StemRegenin I is additionally included with interleukin 7 and interleukin 15, and can be used to directly increase the efficiency of direct reprogramming.

The term "CH-223191" of the second medium is an aryl hydrocarbon receptor inhibitor, and is 1-methyl-N-[2-methyl-4-[2-(2-methylphenyl)diazenyl]phenyl-1H-pyrazole-5-carboxamide. The "aryl hydrocarbon receptor inhibitor" refers to a compound that down-regulates or reduces the activity of the protein encoded by AHR gene or an aryl hydrocarbon receptor, which is a modification thereof, in humans, and if it plays a role of increasing the efficiency of direct reprogramming, it can be used without limitations. For the purpose of the present invention, CH223191, which is an aryl hydrocarbon receptor inhibitor, can be additionally included with StemRegenin I in addition to the cytokine and growth factor of the second medium, and be used to increase the efficiency of direct reprogramming.

Specifically, the first medium and the second medium increase the efficiency of direct reprogramming into promote the production of natural killer cells, and the first medium may comprise cytokine, growth factor, GSK3β inhibitor, StemRegenin I, interleukin 7, and interleukin 15, and the second medium may comprise cytokine, growth factor, StemRegenin I, and CH-223191, but it is not limited thereto if it is a medium composition that directly increases the efficiency of direct reprogramming.

In a specific embodiment of the present invention, it was confirmed that 3-type mixed additives of the first medium (SRI+IL-7+IL-15) had a higher effect of promoting the production of CD56+ and CD3− induced natural killer cells compared to a single additive and 2-type mixed additives. In addition, it was confirmed that the yield of induced natural killer cells was significantly increased in the group treated with aryl hydrocarbon receptor antagonists (StemRegeninI, CH-223191) of the second medium (Example 3).

This suggests that the medium composition of the mixed additives is effective for mass production of induced natural killer cells.

As used herein, the term "reprogramming" refers to a method of converting to a desired cell by controlling the global gene expression pattern, etc. that a specific cell has. In other words, reprogramming of the present invention refers to a method of artificially manipulating the fate of cells to convert them into cells with completely different characteristics, and for the purpose of the present invention, the reprogramming may be performed by introducing a vector containing a foreign gene or DNA into a cell. In one example, reprogramming may include dedifferentiation of cells, direct reprogramming or direct conversion, or transdifferentiation, but is not limited thereto.

As used herein, the term "direct reprogramming" is differentiated from the technique of producing induced pluripotent stem cells having pluripotency through reprogramming, and it is a technique of inducing direct conversion to a desired target cell directly through reprogramming culture. In order to produce natural killer cells, which are target cells, using the existing induced pluripotent stem cell reprogramming technique, first, induced pluripotent stem cells must be prepared from isolated somatic cells, and the hematopoietic stem (progenitor) cells, which are an intermediate, must be differentiated and produced. Since a very complex production culture process of producing natural killer cells, which are the final target cells, differentiated again from hematopoietic stem (progenitor) cells differentiated from induced pluripotent stem cells should be carried out sequentially, there are disadvantages that the production efficiency is low with long time and high cost consumption. In addition, since it is naturally produced through predifferentiated stem cells, whether undifferentiated cells remain and whether safety is secured have become important issues to be verified. However, the present invention is expected to be able to provide an alternative to overcome the problems of the above technique, such as production time, cost, efficiency, safety, etc. by directly producing natural killer cells, which are the target cells, from early cells through the direct reprogramming technique. For the purpose of the present invention, direct reprogramming may be used interchangeably with direct dedifferentiation, direct differentiation, direct conversion, trans-differentiation, cross-differentiation, etc. In the present invention, direct reprogramming may refer to direct dedifferentiation or cross-differentiation particularly into natural killer cells.

As used herein, the term "differentiated cell" refers to a cell having a specialized structure or function. That is, it refers to a state in which cells, tissues, etc. of an organism have been changed to a suitable form and function to perform a role given to each. For example, ectodermal, mesodermal, and endodermal cells derived from predifferentiated stem cells such as embryonic stem cells are differentiated cells, and narrowly, red blood cells, leukocytes, platelets, etc. derived from hematopoietic stem cells are also differentiated cells.

As used herein, the term "intermediate cell" or "natural killer progenitor cell" refers to a cell prior to differentiation into natural killer cells, which may be lymphoid stem cells, but if there is a possibility of differentiation into natural killer cells, it is not limited thereto.

As used herein, the term "natural killer cell" is an important lymphocyte cell responsible for innate immunity and occupies 5% to 10% of all lymphocyte cells, and unlike T cells, it matures in the liver or bone marrow. Natural killer cells are known to be able to differentiate between normal and abnormal cells by expressing various innate immune receptors on the cell surface, and it is also known that they can immediately attach and remove target cells such as virus-infected cells and tumor cells. Natural killer cells that recognize abnormal cells secrete perforin to puncture the cell membrane of the target cell, secrete granzyme into the cell membrane to dissolve the cytoplasm, causing apoptosis, or cause cell necrosis by injecting water and salt into the cell. In addition, as an indirect method, cytokines can be secreted to activate cytotoxic T cells and B cells. While it is known that for the effect of immune action mediated by natural killer cells, the number of natural killer cells and the high activity are very important measures, the development of technology to secure a large number of natural killer cells with high activity is still inadequate.

Due to the characteristics of natural killer cells as described above, the present inventors aimed to produce a large amount of natural killer cells that can be used for the treatment of immune disease and cancer, and as a result, the present inventors have first identified a method that can directly produce a large quantity of natural killer cells through direct reprogramming.

In particular, it was confirmed that natural killer cells produced by the method of the present invention had superior killing potential for various types of cancer cells and superior cytokine secretion potential compared to existing natural killer cells.

Natural killer cells produced by the present invention may express CD56, CD16 or a combination thereof, but are not limited thereto.

The CD56 and CD16 are markers on the surface of natural killer cells, and in the present invention, it was confirmed that natural killer cells were produced by analyzing the expression of CD56, CD16, or a combination thereof through flow cytometry (Example 1).

Another aspect of the present invention is to provide natural killer cells produced according to the above method.

As a result of comparing and analyzing the characteristics of natural killer cells induced through direct reprogramming of the present invention with NK-92, which are existing natural killer cells, and natural killer cells derived from umbilical cord blood, it was confirmed that the natural killer cells of the present invention had excellent proliferation potential (Example 4), excellent killing potential for various cancer cells (Example 8), and excellent cytokine secretion potential (Example 9). Through this, as the natural killer cells produced through the production method of natural killer cells of the present invention have a superior effect compared to existing natural killer cells, it was found that they can be more effectively used in various disease, specifically, cancer treatment, immune disease treatment, etc.

For the purpose of the present invention, natural killer cells produced according to the above method are characterized in expressing specific biomarkers. Specifically, compared to natural killer cells isolated from humans, biomarkers that are specific to the natural killer cells may be to up-express a gene associated with a hematopoietic cell lineage or a gene associated with natural killer cell-mediated cytotoxicity, but are not limited thereto.

The term "gene associated with a hematopoietic cell lineage" generally refers to a gene involved in the process of cell differentiation or formation of blood cells specified from hematopoietic stem cells. Hematopoiesis displaces from the fetal liver to the bone marrow during development, and then the bone marrow remains as a hematopoietic site throughout adulthood. In addition, hematopoietic tissue refers to cells that have long-term and short-term regenerative capacity, as well as multipotent, oligopotent, and monopotent progenitor cells.

In the present invention, the biomarker gene associated with the hematopoietic cell lineage, in which expression is specifically increased in natural killer cells, may be one or more selected from the group consisting of CD71, CD3ε, TNF, M-SCF, CD59, and CD9, but among genes related to the hematopoietic cell lineage, genes in which expression is specifically increased in natural killer cells may be included without limitation.

In addition, the term "natural killer cell-mediated cytotoxicity" refers to the characteristics of recognizing and removing cells infected by a virus or abnormally modified cells through the cytotoxic effect of natural killer cells, and it is stimulated through the cooperation of an activation receptor and an adhesion molecule, and activation signaling means stimulating natural killer cells to secrete cytotoxic granules.

In the present invention, the natural killer cell-mediated cytotoxicity-related biomarker gene with specifically increased expression in natural killer cells may be one or more selected from the group consisting of KIR2DL, KIR2DS, NKp30, FCER1G, ULBP3, SAP, TNFα, INFγ, TRAIL, FAS, and CASP, but among the natural killer cell-mediated cytotoxicity-related genes, genes in which expression is specifically expressed in the natural killer cells may be included without limitation.

In a specific embodiment of the present invention, compared to natural killer cells cultured using an already-known method or natural killer cells (wild type) isolated from humans, it was confirmed that induced natural killer cells produced by the method of the present invention were up-regulated by hematopoietic cell lineage genes associated with differentiation and activity into natural killer cells and natural killer cell-mediated cytotoxicity genes associated with anti-cancer mechanism, and thus it was confirmed that the up-regulated gene functioned as a biomarker (Example 7-3).

Through this, compared to natural killer cells cultured using an already-known culture method or natural killer cells (wild type) isolated from humans, it was found that the induced natural killer cells produced by the method of the present invention were newly isolated natural killer cells having a high degree of activation of natural killer cells.

In addition, the natural killer cells produced according to the above method are characterized in that the characteristics of natural killer cells are maintained even when thawed after cryopreservation.

In one embodiment of the present invention, in order to verify the characteristics of cryopreserved induced natural killer cells, as a result of comparing and analyzing fresh induced natural killer cells and the aspect of cell surface receptor expression using flow cytometry (FACS) after thawing, it was confirmed that the characteristics of the cells did not change after cryopreservation, by confirming that the expressions of CD56, CD16, CD69, DNAM-I, NKG2D, NKp46, etc. were similar in fresh induced natural killer cells and cryopreserved induced natural killer cells (Example 11).

Still another aspect of the present invention is to provide a cell therapeutic agent comprising the natural killer cells produced according to the above method as an active ingredient.

As used herein, the term "cell therapeutic agent" is a medicine (US FDA regulation) used for the purpose of treatment, diagnosis, and prevention with cells and tissues prepared through isolation, culture, and special manipulation from a subject. It refers to a medicine that is used for the purpose of treatment, diagnosis, and prevention through a series of action such as proliferation screening of living autologous, allogeneic, or xenogeneic cells ex vivo to restore the function of cells or tissues, or other methods to change the biological properties of cells.

Still another aspect of the present invention is to provide a pharmaceutical composition for treating or preventing cancer, comprising the natural killer cells prepared according to the above method as an active ingredient.

The cancer may be cancer showing the results of treatment or prevention by the immune response of natural killer cells, etc., and specifically, it may be pancreatic cancer, lung cancer, ovarian cancer, breast cancer, colon cancer, bone marrow cancer, liver cancer, brain cancer, prostate cancer, stomach cancer, colon cancer, glioma, melanoma, lymphoma, rectal cancer, blood cancer, but is not limited thereto.

In addition, it is known that natural killer cells have an effect of treatment or prevention for prostate cancer (Liu (2013), *J Clin Invest* 123 (10): 4410-4422), and stomach cancer, colon cancer, glioma, melanoma, lymphoma, and rectal cancer (Dahlberg (2015), *Front Immunol* 6: 605).

In addition, the composition is characterized by having a killing potential against cancer stem cells.

In a specific embodiment of the present invention, after reacting induced natural killer cells and each of SW620 and HCT116 cancer cells, which are colon cancer cells, and reacting the induced natural killer cells and each cancer stem cell at a ratio of 1:1 for four hours, as a result of measuring the expression of CD107a, which is an indicator of killing potential, by flow cytometry (FACS), it was confirmed that the expression of the induced natural killer cells was higher in cancer stem cells for cancer cells of SW620 and HCT116 and cancer stem cells, respectively (Example 8-3).

Through this, it suggests that the induced natural killer cells have a higher killing potential in cancer stem cells as well as cancer cells.

As used herein, the term "prevention" refers to any action that inhibits or delays the development of cancer by administration of the composition.

As used herein, the term "treatment" refers to any action by which symptoms caused by cancer are improved or ameliorated by administration of the composition.

The composition may comprise a pharmaceutically acceptable carrier.

The term "pharmaceutically acceptable carrier" may refer to a carrier or diluent that does not inhibit the biological activity and properties of the compound to be injected without stimulating the organism. The type of the carrier that can be used in the present invention is not particularly limited, and any carrier that is conventionally used and is pharmaceutically acceptable can be used. Non-limiting examples of the carrier include saline, sterile water, Ringer's solution, buffered saline, albumin injection solution, dextrose solution, maltodextrin solution, glycerol, ethanol, etc. These may be used alone or in combination of two or more.

The composition comprising a pharmaceutically acceptable carrier may be various oral or parenteral formulations. In the case of formulation, it is prepared using diluents or excipients such as fillers, extenders, binders, wetting agents, disintegrating agents, surfactants, etc.

Specifically, solid preparations for oral administration include tablets, pills, powders, granules, capsules, etc., and these solid preparations may be prepared by mixing at least one excipient with the compound, for example, starch, calcium carbonate, sucrose, lactose, gelatin, etc. In addition, lubricants such as magnesium stearate and talc may be used in addition to simple excipients. Liquid preparations for oral use include suspending agents, intravenous solutions, emulsions, syrups, etc., and in addition to commonly used simple diluents such as water and liquid paraffin, various excipients such as wetting agents, sweeteners, fragrances, preservatives, etc. may be included. Preparations for parenteral administration include sterile aqueous solutions, non-aqueous solutions, suspensions, emulsions, lyophilized preparations, and suppositories. For non-aqueous solvents and suspending agents, propylene glycol, polyethylene glycol, vegetable oils such as olive oil, injectable esters such as ethyl oleate, etc. may be used. As bases for suppositories, witepsol, macrogol, tween 61, cacao butter, laurin butter, and glycerogelatin may be used.

The composition may be administered in a pharmaceutically effective amount.

The term "pharmaceutically effective amount" refers to an amount sufficient to treat a disease at a reasonable benefit/risk ratio applicable to medical treatment, and effective dose levels may be determined depending on the type of a subject, severity, age, gender, type of virus infected, drug activity, sensitivity to the drug, duration of administration, rate of administration and excretion, duration of treatment, factors including concurrently used drugs, and well-known factors in other medical fields. For example, the composition or a pharmaceutically acceptable salt thereof may be administered at 0.0001 mg/kg to 1,000 mg/kg per day, preferably 0.001 mg/kg to 100 mg/kg.

The administration refers to introducing the composition of the present invention to a patient in any appropriate method, and the administration route of the composition can be administered through any general route as long as it can reach the target tissue. It can be administered via intraperitoneal administration, intravenous administration, intramuscular administration, subcutaneous administration, intradermal administration, oral administration, topical administration, and intranasal administration, but is not limited thereto.

The composition of the present invention may be administered daily or intermittently, and the number of administrations per day may be once or divided into two to three times. When the two active ingredients are single agents, the number of administration may be the same or may be different. In addition, the composition of the present invention can be used alone or in combination with other drug treatments for the prevention or treatment of cancer. Considering all of the above factors, it is important to administer an amount that can achieve the maximum effect in a minimal amount without side effects, and the amount can be determined by those skilled in the art.

The subject refers to all animals including humans, monkeys, cows, horses, sheep, pigs, chickens, turkeys, quails, cats, dogs, mice, rats, rabbits, or guinea pigs that may have developed cancer or are likely to develop cancer. If the disease can be effectively prevented or treated by introducing the pharmaceutical composition of the present invention to a subject, the type of the subject is included without limitation.

Another aspect of the present invention is to provide a method for preventing or treating cancer, comprising administrating the pharmaceutical composition to a subject in need thereof.

The "subject", "administration", "cancer", and "treatment" are the same as described above.

In one specific embodiment of the present invention, it was confirmed that natural killer cells produced by direct reprogramming of the present invention had excellent killing potential against various cancer cells of pancreatic cancer, lung cancer, ovarian cancer, breast cancer, colon cancer, bone marrow cancer, liver cancer, brain cancer, or blood cancer, and as a result of the comparative experiment of the cancer cell killing potential of existing natural killer cells, it was confirmed that the cancer cell ability of the natural killer cells of the present invention was much more excellent (Example 8).

Through this, it can be seen that natural killer cells produced through direct reprogramming of the present invention are more excellent in cancer cell treatment than existing natural killer cells.

Still another aspect of the present invention is to provide a method for preparing a cell vial for cryopreservation, comprising (a) introducing a reprogramming factor into isolated cells; and (b) culturing the cells of step (a) in i) a first medium comprising cytokine, growth factor, and GSK3β inhibitor, and ii) a second medium comprising cytokine and growth factor to directly reprogram into natural killer cells.

In addition, the cell vial for cryopreservation prepared according to the above method provides a cell vial for cryopreservation in which the characteristics of natural killer cells are maintained upon thawing after cryopreservation.

The "isolated cells", "reprogramming factor", "cytokine", "growth factor", "GSK3β inhibitor", "culture", "natural killer cell" and "direct reprogramming" are the same as described above.

As used herein, the term "cryopreservation" refers to maintaining cells stable over a long period of time through freezing. In cells, mutations generally occur at a ratio of 1 in 10,000 in culture, and if the cell passage is continued for a long period of time, it changes into a cell population that is different from the original cell population, and in some cases, a specific function of the cell is lost by passage culture. In addition, it may be infected with mycoplasma during passage culture. Due to such problems, cells are frozen before the intrinsic properties of the cells are lost and preserved, and cryopreservation of the cells is performed so that the cells can be taken out and used as needed. In particular, in the case of stem cells, effective cryopreservation is considered to be more important in stem cells, because healthy stem cells must be readily available for use as a therapeutic agent. Cryopreservation may be performed through conventional methods in the art of freezing and preserving cells, and examples include the vitrification method or the slow freezing method, but are not limited thereto.

As used herein, the term "vial" refers to a container used when a cryopreservative solution is divided and used. The vial is sealed and preserved in a sterile state, but is not limited thereto.

In addition, the cell cryopreservation method may be performed by including cells in an appropriate concentration in the vial. The concentration of cells contained in the vial may be $1 \times 10^4$ cells/mL to $1 \times 10^8$ cells/mL, but is not limited thereto, and particularly, it may be $1 \times 10^8$ cells/mL.

In one specific embodiment of the present invention, in order to verify the characteristics of the cryopreserved induced natural killer cells, after thawing, fresh induced natural killer cells and cell surface receptor expression patterns were compared and analyzed using flow cytometry (FACS).

As a result, by confirming that the expressions of CD56, CD16, CD69, DNAM-I, NKG2D, NKp46, etc. were similar in fresh induced natural killer cells and cryopreserved induced natural killer cells, it was confirmed that the characteristics of the cells did not change after cryopreservation (Example 11).

Through this, it suggests that the characteristics of natural killer cells are maintained even upon thawing after cryopreservation using the cell vial for cryopreservation prepared by the above preparation method.

Still another aspect of the present invention is to provide a medium kit for inducing direct reprogramming, comprising a first container comprising a first medium of cytokine, growth factor, GSK3β inhibitor, StemRegenin I, interleukin 7, and interleukin 15; and a second container comprising a second medium of cytokine, growth factor, StemRegenin I, and CH-223191.

The "cytokine", "growth factor", "GSK3β inhibitor", "medium", "StemRegenin I", "CH-223191", "interleukin 7", and "interleukin 15" are the same described above.

As used herein, the term "medium kit" is a device comprising a medium composition necessary for cell culture comprising any exemplary embodiment. The medium kit of the present invention comprises a first container comprising the first medium; and a second container comprising a second medium, and the efficiency of direct reprogramming can be increased by sequentially using the first container and the second container.

DETAILED DESCRIPTION

Hereinafter, the present invention will be described in more detail through examples and experimental examples. However, these examples and experimental examples are for illustrative purposes only, and the scope of the present invention is not limited to these examples and experimental examples.

Example 1: Direct Reprogramming from PBMC to Natural Killer Cells

After culturing isolated peripheral blood mononuclear cells (PBMC) for 4 days in a culture solution by changing the medium once every two days, CD34-positive cells and CD56-positive cells were removed from whole peripheral blood mononuclear cells using the magnetic activated cell sorting (MACS) technique using CD34 isolation microbeads kit (Miltenyl Biotec) and CD56 isolation microbeads kit (Miltenyl Biotec), and PBMC (CD34$^-$CD56$^-$) cells were removed from which immune cells such as NK cells, etc. were removed.

Figure 1:
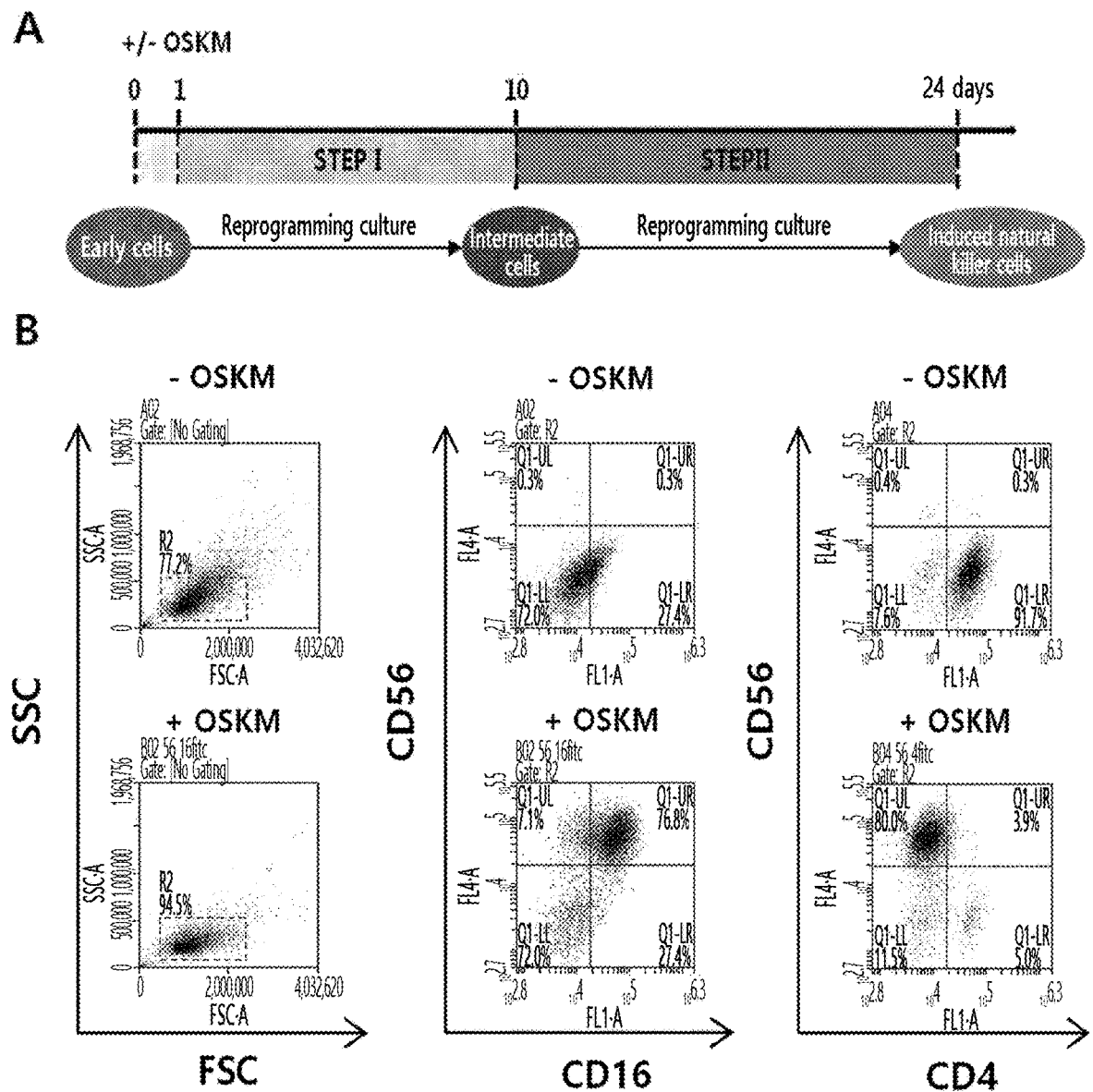

A virus system (Oct4, Sox2, Klf4, and Myc-expressing RNA-based Sendai virus (CytoTune 2.0 Sendai reprogramming kit, Thermo Scientific)) was used for the isolated PBMC (CD34$^-$CD56$^-$) cells to transform reprogramming factors (Oct4, Sox2, Klf4, and Myc) (FIG. 1A).

Specifically, in order to transform the reprogramming factor, the virus (5 MOI, based on KOS), isolated PBMC (CD34$^-$CD56$^-$) cells, and polybrene (4 µg/mL) were cultured together for one day, and then replaced with a fresh medium after culture.

The next day, $2\times10^5$ of the transformed cells were cultured for 9 days in a 24-well culture plate in NKIM-I medium (StemSpan SFEM II including 10% FBS, 1% Penicillin/Streptomycin, 5 µM CT 99021, 20 ng/ml Human IL-3, 20 ng/ml Human IL-6, 20 ng/ml Human SCF, 20 ng/ml Human FLT3, 20 ng/ml Human TPO) (FIG. 1A; STEP I). On the $10^{th}$ day of culture, after isolating a colony (natural killer cell precursors) formed in the culture, the isolated colony was cultured for 14 days in NKIM-II medium (StemSpan SFEM II including 10% FBS, 1% Penicillin/Streptomycin, 25 ng/ml Human IL-2, 20 ng/ml Human IL-7 20 ng/ml Human IL-15, 20 ng/ml Human SCF, 20 ng/ml Human FLT3, 2 µM StemRegenin I) to induce to natural killer cells (FIG. 1A; STEP II).

In order to confirm that natural killer cells were produced through the direct reprogramming, after staining the cells with CD56, CD16, or CD4, which is a marker for natural killer cells, the group of natural killer cells (CD56$^+$ and CD16$^+$ or CD56$^+$ and CD4$^-$) was analyzed using flow cytometry (FACS).

Specifically, after reacting the induced cells that were isolated from single cells in an FACS buffer (phosphate buffer including 1% BSA, 2 mM EDTA) added with fluorescently-attached antibodies against CD56, CD16, and CD4 attached with fluorescence for 20 minutes at room temperature, the cells were washed and recovered using a centrifuge, and then analyzed by FACS (BD Bioscience).

It was confirmed that peripheral blood mononuclear cells, into which reprogramming factors (Oct4, Sox2, Klf4, and Myc) were introduced, were directly induced into human natural killer cells by direct reprogramming (FIG. 1A).

In a control group that did not transform the reprogramming factor, whereas the cell group expressing the natural killer cell indicator was 0.3%, it was confirmed that about 80% was a cell group that expressed a natural killer cell indicator in the experimental group (FIG. 1B).

Through this, it was confirmed that natural killer cells were produced by direct reprogramming by introduction of reprogramming factors.

Example 2: Role of GSK3β in Direct Reprogramming from PBMC to Natural Killer Cells In order to confirm the role of CT99021, a GSK3β inhibitor, included in NKIM-I in Example 1, after recovering PBMC (CD34$^-$CD56$^-$) cells, comparative experiments were performed for a case where CT99021 was added to the cells in NKIM-I medium (StemSpan SFEM II including 10% FBS, 1% Penicillin/Streptomycin, 5 µM CT99021, 20 ng/ml Human IL-3, 20 ng/ml Human IL-6, 20 ng/ml Human SCF, 20 ng/ml Human FLT3, 20 ng/ml Human TPO) and a case where it was not added on day 1.

On the $24^{th}$ day when direct reprogramming was started as in Example 1, the cells were recovered and stained using antibodies against CD56 and CD4 attached with fluorescence and then the group of natural killer cells (CD56$^+$ and CD4$^-$) was analyzed by flow cytometry.

Figure 2:
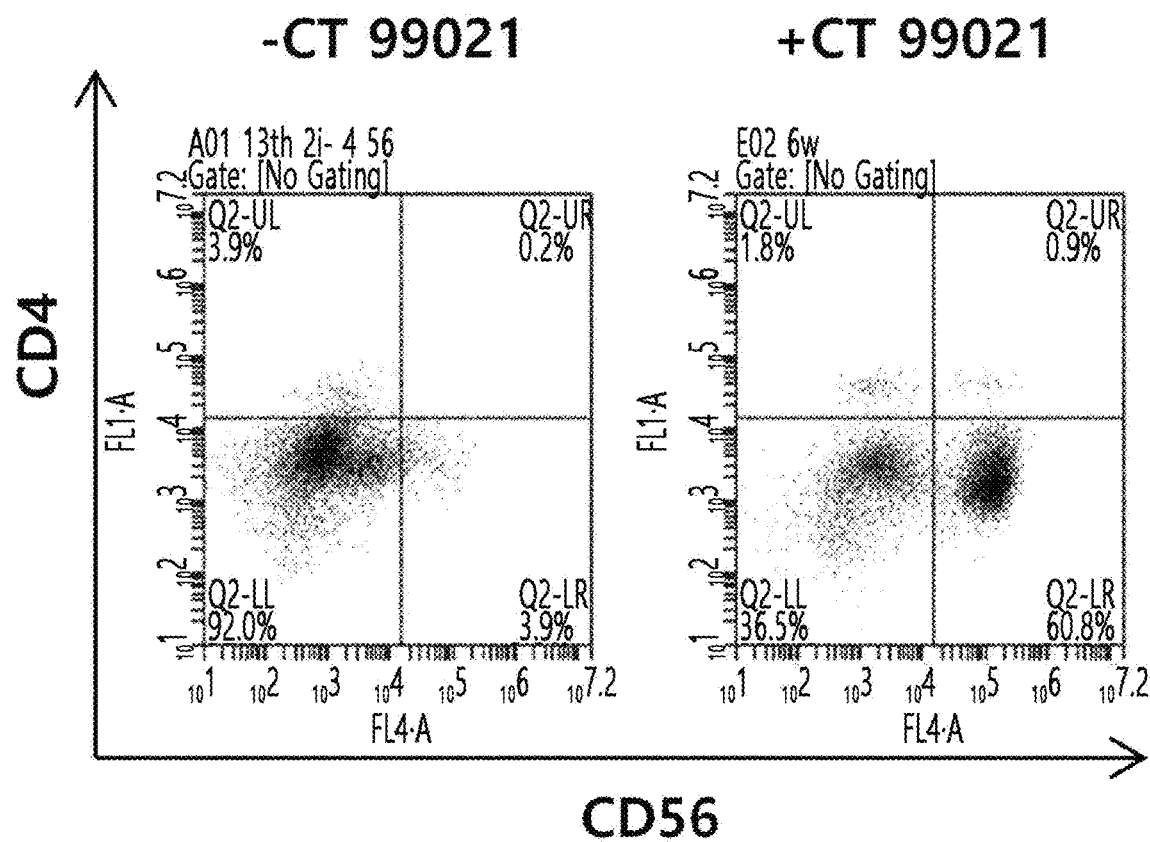
FIG. 2 is a diagram showing the effect of GSK3β inhibitor.

As a result, when CT99021 was not added, it was confirmed that the differentiation into natural killer cells was significantly lowered (FIG. 2). This suggests that CT99021 plays an important role at the beginning step of direct reprogramming to natural killer cells.

Example 3: Efficiency of Direct Reprogramming Depending on Compositions of NKIM-I Medium and NKIM-II Medium After introducing reprogramming factors (Oct4, Sox2, Klf4, and Myc) into PBMC cultured in the NKIM-I medium and NKIM-II medium, a mixture additive was added to the medium for analysis to promote the production capacity of natural killer cells produced by direct reprogramming.

Example 3-1: Efficiency of Direct Reprogramming Depending on Composition of NKIM-I Medium Specifically, in the case of NKIM-I medium, after introducing OSKM into PBMC, the following day, $1\times10^5$ transformed cells were added to a 48-well culture dish in the reprogramming culture process with different combinations of 5 µM CHIR 99021, 2 mM LiCl, 20 ng/mM, 2 µM StemRegenin I, human IL-7, and 20 ng/mL human IL-15 in NKIM-I medium, and the production capacity of CD56+ induced natural killer cells was thereby confirmed.

Figure 3A:
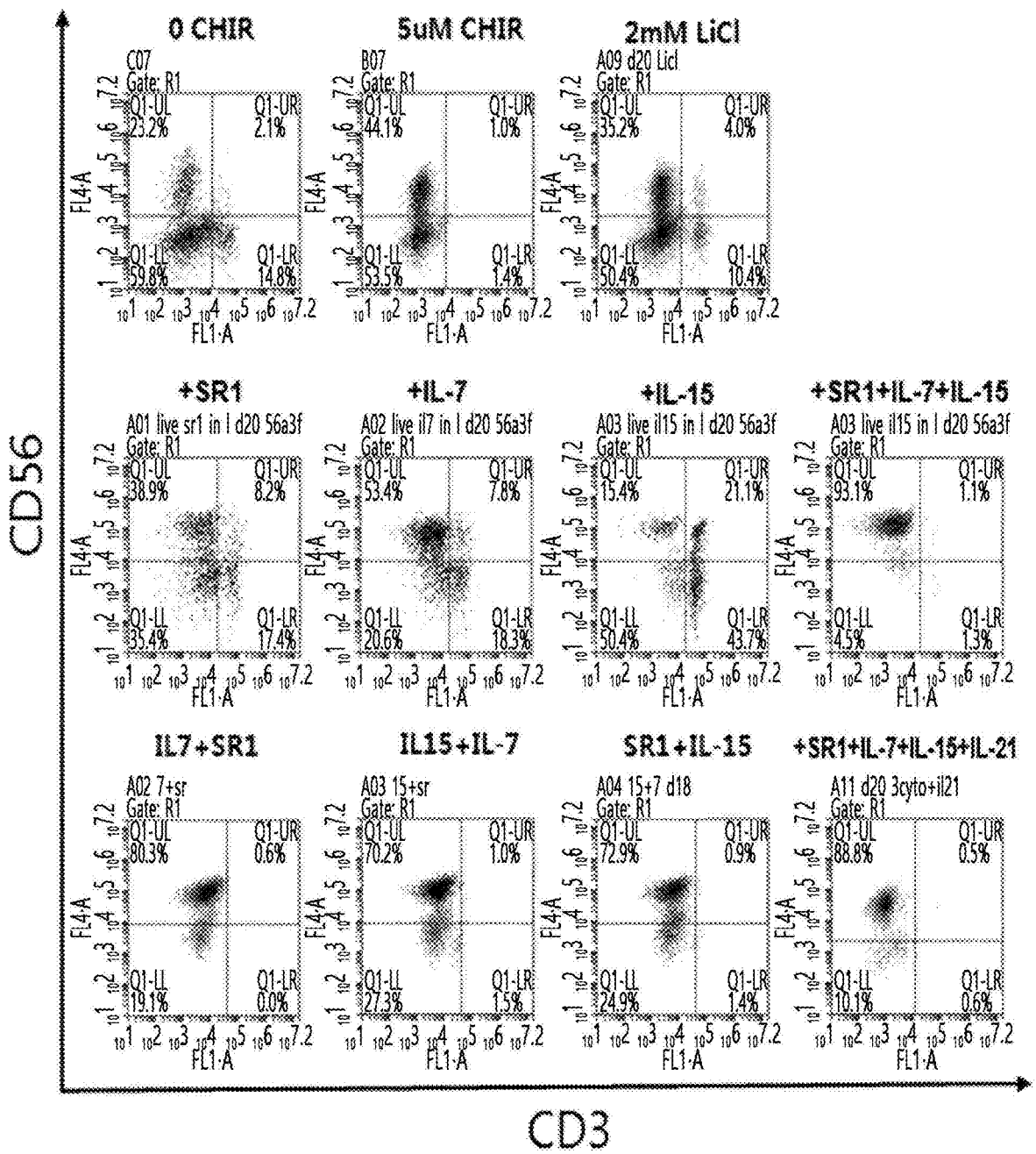
FIG. 3A is a diagram showing the efficiency of direct reprogramming depending on the composition of NKIM-I medium.

As a result, when each of CHIR 99021, LiCl, StemRegenin I, IL-7, and IL-15 additives was added by comparing with the condition without additives, it was confirmed that there was an effect of promoting the production of CD56+ CD3− induced natural killer cells, and it was also confirmed that 2-type mixed additives, IL7+SRI, IL15+IL-7, and SRI+ IL-15, and a 3-type mixed additive of SRI+IL-7+IL15 had higher production promoting effect compared to single additives (FIG. 3A).

Example 3-2: Efficiency of Direct Reprogramming Depending on Composition of NKIM-II Medium In the case of NKIM-II medium, after introducing OSKM into PBMC cells, the following day, $1\times10^5$ transformed cells were added to a 48-well culture dish and cultured in NKIM-I medium for 6 days, and then these cells were cultured for 29 days in a medium in which StemRegenin I, which is an aryl hydrocarbon receptor antagonist, CH-223191, or FICZ, which is an aryl hydrocarbon receptor agonist, was added to NKIM-II.

Figure 3B:
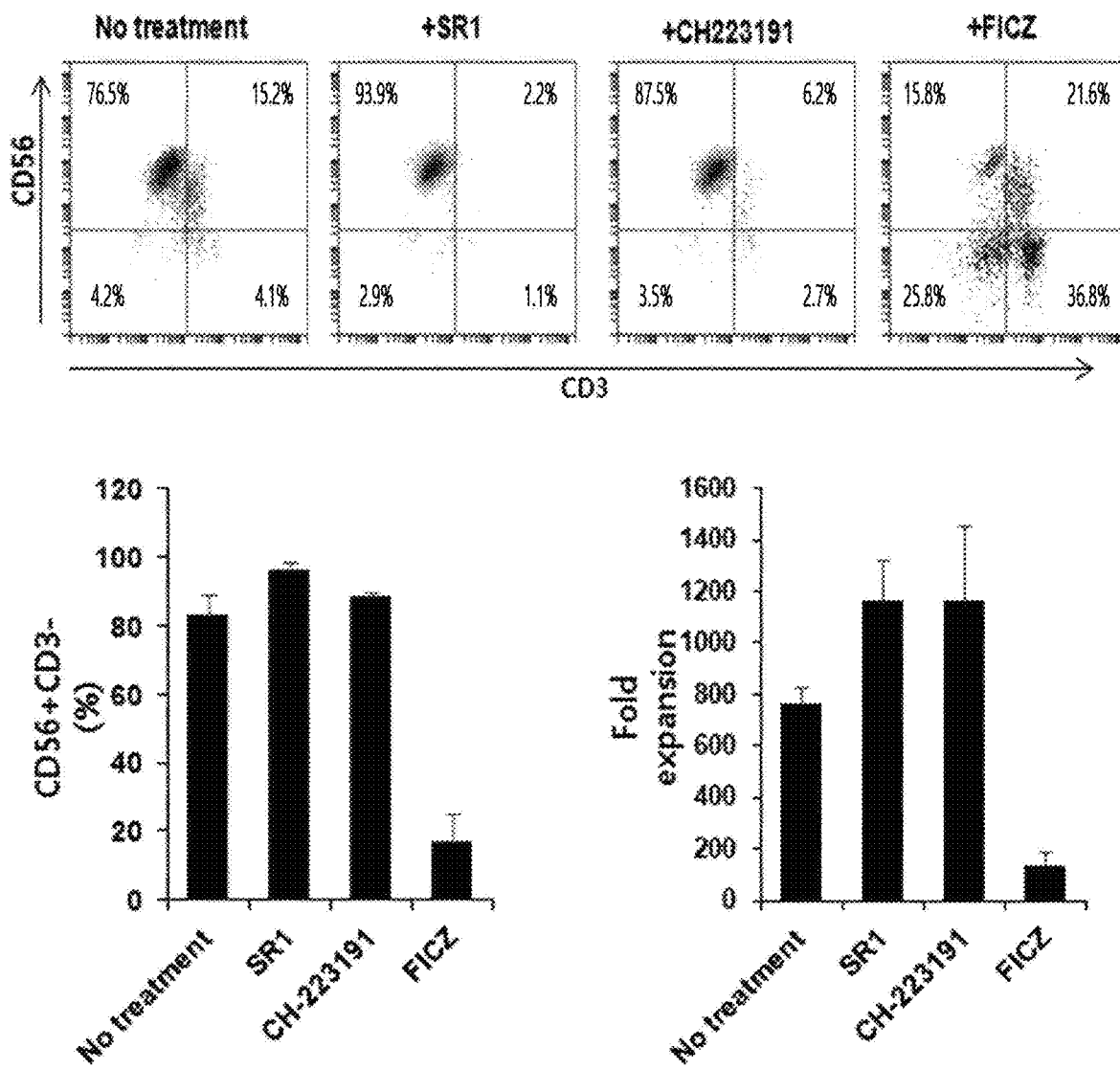
FIG. 3B is a diagram showing the efficiency of direct reprogramming depending on the composition of NKIM-II medium.

As a result, it was confirmed that the yield of induced natural killer cells was significantly increased in the group treated with an aryl hydrocarbon receptor agonist (StemRegenin I, CH-223191). When FICS, which is an aryl hydrocarbon receptor agonist, was added, it was confirmed that the yield of induced natural killer cells was significantly reduced (FIG. 3B).

Through this, the yield of induced natural killer cells produced by the present invention was related to the composition of the medium, and when the mixture was added to the NKIMI-medium or the antagonist was treated in NKIM-II medium, the increased production capacity of induced natural killer cells was confirmed, and through this, it was found that the medium composition was effective for mass production of induced natural killer cells.

Example 4: Measurement of Proliferation Potential of Directly Reprogrammed Natural Killer Cells The following experiment was performed to evaluate the proliferation potential of natural killer cells produced by the present invention.

Specifically, the proliferation potential of cells, in which the lineage induced by NKIM-I medium was transformed as in Example 1, was confirmed by exchanging the NKIM-II medium (StemSpan SFEM II including 10% FBS, 1% Penicillin/Streptomycin, 25 ng/ml Human IL-2, 20 ng/ml Human IL-7 20 ng/ml Human IL-15, 20 ng/ml Human SCF, 20 ng/ml Human FLT3, 2 µM StemRegenin I) with a fresh medium every three days, and measuring the growth rate using a Hemocytometer for 39 days, and as a result, in the case of the experimental group in which the reprogramming factor was transformed, it was confirmed that it increased by about 1,200 times compared to the initial cell number on the $49^{th}$ day (FIG. 4A).

As in Example 1, after staining the experimental group and the control group using antibodies against CD56 and CD16 attached with fluorescence, the group of natural killer cells (CD56+ and CD16+) was analyzed by flow cytometry.

As a result, in the case of the control group, whereas the cell group, which was positive for CD56, a natural killer cell indicator, was 0.3%, 93.6% was confirmed to be a group of natural killer cells, which were CD56 positive in the experimental group (FIG. 4B).

Through this, as the natural killer cells produced by the present invention have excellent proliferation potential, it is expected to be useful for mass production of natural killer cells.

Example 5: Measurement of Proliferation Potential Depending on Reprogramming Factors In order to determine the combination condition of minimum reprogramming factors for inducing natural killer cells by reprogramming, different combinations of Oct4, Sox2, Klf4, and Myc factors were introduced into peripheral blood mononuclear cells, and the following experiment was performed to confirm that natural killer cells were induced by direct reprogramming.

Specifically, PBMC cells as in Example 1 were each transformed with reprogramming factor combinations of four sets (a: Klf4, Oct4, and Sox2; b: Klf4 and Myc; c: Klf4; d: Myc).

The next day, $2 \times 10^5$ cells transformed with each set were cultured in NKIM-I medium (StemSpan SFEM II including 10% FBS, 1% Penicillin/Streptomycin, 5 µM CT99021, 20 ng/ml Human IL-3, 20 ng/ml Human IL-6, 20 ng/ml Human SCF, 20 ng/ml Human FLT3, 20 ng/ml Human TPO) in a 24-well culture dish for 9 days. On the $10^{th}$ day of culturing, after isolating colonies (cells in which the lineage had been converted) formed in the culture, the isolated colonies were cultured in NKIM-II medium (StemSpan SFEM II including 10% FBS, 1% Penicillin/Streptomycin, 25 ng/ml Human IL-2, 20 ng/ml Human IL-7 20 ng/ml Human IL-15, 20 ng/ml Human SCF, 20 ng/ml Human FLT3, 2 µM StemRegenin I) for 18 days.

As a result, even when all of the reprogramming factors, Oct4, Sox2, Klf4, and Myc were not introduced, it was confirmed that natural killer cells were produced (FIG. 5).

Example 6: Direct Reprogramming from Various Cells to Natural Killer Cells

The following experiment was performed to confirm that natural killer cells induced by direct programming could be produced using cells other than peripheral blood mononuclear cells.

Specifically, it was confirmed that human skin fibroblasts or human dental pulp cells transformed with reprogramming factors (Oct4, Sox2, Klf4, and Myc) were induced into natural killer cells by direct reprogramming (FIG. 6).

The human skin fibroblasts or human dental pulp cells were each cultured by two methods (FIG. 5A; a and b) to induce to natural killer cells (FIG. 6A). Commonly, after culturing for 4 days in FF medium (MEM-α medium including FBS 15%), the cells were transformed with four reprogramming factors (Oct4, Sox2, Klf4, and Myc) as in Example 1. After transformation, the cells were cultured in IM-I medium (DMEM/F12 including FBS 5%, KSR 10%, NEAA 1%, β-mercaptoethanol 0.11 mM, bFGF 10 ng/ml, CT99021 3 µM, Na-butyrate 0.1 mM, Parnate 2 µM, RG108 0.5 µM, NECA 0.5 µM).

Afterwards, in the case of a, after culturing in IM-II medium (Stempro-34 medium including StemPro-34 supplement, Ascorbate 1 mM, MTG 1 mM, Glutamax-I 1%, Human transferrin 150 ug/ml, SB431542 6 µM, CT99021 3 µM, IL-3 30 ng/ml, IL-6 10 ng/ml, IL-11 5 ng/ml, SCF 50 ng/ml, FLT3 10 ng/ml, TPO 30 ng/ml, EPO 2U) for 11 days, on the $16^{th}$ day of culturing, colonies (natural killer cell precursors) formed in the culture were isolated, and the isolated colonies were cultured in NKIM-II medium (StemSpan SFEM II including 10% FBS, 1% Penicillin/Streptomycin, 25 ng/ml Human IL-2, 20 ng/ml Human IL-7 20 ng/ml Human IL-15, 20 ng/ml Human SCF, 20 ng/ml Human FLT3, 2 µM StemRegenin I) for 14 days.

In the case of method b, after culturing in IM-III medium (IMDM/F12=75%/25% containing N2 0.5%, B27 1%, BSA 0.05%, Ascorbate 1 mM, MTG 1 nM, Glutamax-I 1%, Human transferrin 150 ug/ml, BMP4 50 ng/ml, bFGF 5 ng/ml, SB431542 6 µM, CT99021 3 µM) for 2 days, the cells were cultured in the IM-II medium (Stempro-34 including StemPro-34 supplement, Ascorbate 1 mM, MTG 1 nM, Glutamax-I 1%, Human transferrin 150 µg/ml, SB431542 6 µM, CT99021 3 µM, IL-3 30 ng·ml, IL-6 10 ng/ml, IL-11 5 ng/ml, SCF 50 ng/ml, FLT3 10 ng/ml, TPO 30 ng/ml, EPO 2U) for nine days. Afterwards, on the $16^{th}$ day of culturing, colonies (cells in which the lineage had been converted) formed in the culture were isolated, the isolated colonies were cultured in NKIM-II medium (StemSpan SFEM-II including 10% FBS, 1% Penicillin/Streptomycin, 25 ng/ml Human IL-2, 20 ng/ml Human IL-7 20 ng/ml Human IL-15, 20 ng/ml Human SCF, 20 ng/ml Human FLT3, 2 µM StemRegenin I) for 14 days.

After human skin fibroblasts or human dental pulp cells cultured by the above method a or method b were stained using an antibody against CD56 attached with fluorescence as in Example 1, a group of natural killer cells (CD56+) were analyzed by flow cytometry.

As a result, in the case of human skin fibroblasts, it was confirmed that the cell group with CD56 positive, which is a natural killer cell indictor, was 71.7% in the case of method a, and the cell group with CD56 positive was 58.6% in the case of method b (FIG. 6B). In addition, in the case of human dental pulp cells, it was confirmed that the cell group with CD56 positive, a natural killer cell indicator, was 42.4%, and the cell group with CD56 positive was 32.7% in the case of method b (FIG. 6C).

Example 7: Measurement of Activity of Natural Killer Cells

Example 7-1: Measurement of Expression Patterns of Specific Markers of Natural Killer Cells As in Example 1, for the cells induced by the NKIM-I medium, in which the lineage had been converted, the expressions of activation and inhibitory receptors related to various natural killer cells were analyzed in cells cultured in NKIM-II medium for 28 days using a flow cytometer. It was confirmed that activation receptors such as CD16, NKG2D, NKp46, NKG2A, and DNAM1 and inhibitory receptors such as KIR2DL1, KIR3DL1, KIR2DL4, etc. showed high frequency expression (FIG. 7).

Example 7-2: Comparative Experiment with Natural Killer Cells Derived from Umbilical Cord Blood Cells After obtaining CB-CD3 from which CD positive T cells had been removed using Rosettsep from umbilical cord blood (CB), the initial concentration was set at $1 \times 10^6$ cells/mL, and the cells were suspended in α-MEM including 1% penicillin/streptomycin, 10 ng/mL human IL-21, 10 ng/mL human IL-15, and 10 nM hydrocortisone, and the culture began in a T75 flask. Every two to three days, it was replaced with a new medium, and the differentiation of natural killer cells was measured through measurement of the number of cells and measurement of indicators such as CD3, CD56, etc., to confirm the differentiation of natural killer cells every two to three weeks.

As in Example 1, for cells that were induced by NKIM-1 medium, in which lineage had been converted, the expressions of activation and inhibitory receptors (CD16, NKG2D, NKp46, NKG2A, DNAM1, KIR2DL1, KIR3DL1, and KIR2DL4) related to various natural killer cells were comparatively analyzed in cells cultured for 28 days in NKIM-II medium and CB-natural killer cells (CB-NK) obtained from umbilical cord blood as described above. As a result, similar to natural killer cells derived from umbilical cord blood cells, it was confirmed that natural killer cell-specific marker receptors were significantly expressed in the induced natural killer cells of the present invention (FIG. 8).

Example 7-3: Specific Biomarkers of Induced Natural Killer Cells

The expression characteristics and differences of the cell surface receptors of peripheral blood natural killer cells and induced natural killer cells were analyzed using a flow cytometer to analyze the expression patterns of CD56, CD16, CD69, NKG2D, DNAM-I, NKp46, NKG2A, KIR2DL2/3, KIR2DL1, KIR3DL1, etc. Specifically, compared to natural killer cells that naturally exist in peripheral blood, the expressions of CD69 and NKG2D, which indicate the degree of activation of natural killer cells in the induced natural killer cells, were confirmed to be significantly higher. Therefore, it was confirmed that the induced natural killer cells had the properties of CD56+, CD3−, CD16+, CD69+, and NKG2D+ (FIGS. 9A and 9B).

In addition, cDNA microarray gene chip analysis was performed to see the global gene expression patterns of primary cultured natural killer cells (pNK, wild type) and induced natural killer cells (iNK) (28 days). Among all of 21,488 genes, 1,523 genes showing up to two times more significant differences were identified by up- or down-regulation between two groups (FIG. 9C). Overall, it was confirmed that the genes for cell division and immune response were up-regulated in the induced natural killer cells, and the genes related to cell signaling were down-regulated. Genes that were up-regulated by about 15 times or more only in induced natural killer cells were identified (Table 1), the expression differences of genes associated with hematopoietic cell lineage, CD71 (3.1 fold), CD3ε (4.5 fold), TNF (7.1 fold), M-SCF (44.0 fold), CD59 (3.1 fold), and CD9 (4.5 fold) were confirmed, and the expression differences of genes associated with natural killer cell-mediated cytotoxicity, KIR2DL (8.7 fold), KIR2DS (4.7 fold), NKp30 (2.8 fold), FCER1G (2.0 fold), ULBP3 (2.2 fold), SAP (2.2 fold), TNFα (7.1 fold), IFN γ (3.1 fold), TRAIL (5.9 fold), FAS (3.6 fold), and CASP (2.6 fold) were confirmed (Table 2).

Through this, compared to primary culture natural killer cells, it was confirmed that the hematopoietic cell lineage genes associated with differentiation into and activity of natural killer cells; and the natural killer cell-mediated cytotoxicity genes associated with the anti-cancer mechanism were up-regulated in the induced natural killer cells of the present invention, and it was confirmed that the up-regulated genes functioned as biomarkers. In addition, it was confirmed that the induced natural killer cells enhanced the effect of cancer cell killing potential through regulation of the genes.

TABLE 1

| Gene symbol | mRNA receptor | Fold difference | Gene description |
| --- | --- | --- | --- |
| DPP4 | NM_001935 | 60.1 | dipeptidyl-peptidase 4 |
| CSF1 | NM_000757 | 44.1 | colony stimulating factor 1 (macrophage) |
| DLGAP5 | NM_001146015 | 33.3 | discs, large (*Drosophila*) homolog-associated protein 5 |
| DDX3Y | NM_001122665 | 31.2 | DEAD (Asp-Glu-Ala-Asp) box helicase 3, Y-linked |
| FAM72C | NM_001287385 | 29.9 | family with sequence similarity 72, member C |
| FAM72A | NM_001123168 | 29.3 | family with sequence similarity 72, member A |
| TMEM200A | NM_001258276 | 27.4 | transmembrane protein 200A |
| FAM72B | NM_001100910 | 26.4 | family with sequence similarity 72, member B |
| BUB1 | NM_001278616 | 23.7 | BUB1 mitotic checkpoint serine/threonine kinase |
| CDKN3 | NM_001130851 | 22.5 | cyclin-dependent kinase inhibitor 3 |
| FAM72D | NM_207418 | 21.6 | family with sequence similarity 72, member D |
| E2F8 | NM_001256371 | 19.9 | E2F transcription factor 8 |

TABLE 1-continued

| Gene symbol | mRNA receptor | Fold difference | Gene description |
|---|---|---|---|
| EIF1AY | NM_001278612 | 19.7 | eukaryotic translation initiation factor 1A, Y-linked |
| ARHGAP11B | NM_001039841 | 19.6 | Rho GTPase activating protein 11B |
| CCR5 | NM_000579 | 19.1 | chemokine (C-C motif) receptor 5 (gene/pseudogene) |
| NUF2 | NM_031423 | 18.3 | NUF2, NDC80 kinetochore complex component |
| TTK | NM_001166691 | 17.6 | TTK protein kinase |
| NDC80 | NM_006101 | 17.3 | NDC80 kinetochore complex component |
| ANLN | NM_001284301 | 17.1 | anillin actin binding protein |
| NDFIP2 | NM_001161407 | 17.0 | Nedd4 family interacting protein 2 |
| NCAPG | NM_022346 | 16.9 | non-SMC condensin I complex subunit G |
| STX3 | NM_001178040 | 16.8 | syntaxin 3 |
| KIF2C | NM_001297655 | 16.8 | kinesin family member 2C |
| CDK1 | NM_001170406 | 16.2 | cyclin-dependent kinase 1 |
| KIF18A | NM_031217 | 15.9 | kinesin family member 18A |
| KIAA0101 | NM_001029989 | 15.3 | KIAA0101 |
| CEP55 | NM_001127182 | 15.2 | centrosomal protein 55 kDa |
| SGOL1 | NM_001012409 | 15.0 | shugoshin-like 1 (S. pombe) |
| CASC5 | NM_144508 | 14.9 | cancer susceptibility candidate 5 |
| SLC27A2 | NM_001159629 | 14.7 | solute carrier family 27 (fatty acid transporter), member 2 |

TABLE 2

| Hematopoietic cell lineage KEGG | | Hematopoietic cell lineage KEGG | |
|---|---|---|---|
| Gene symbol | Fold difference | Gene symbol | Fold difference |
| CSF1 | 44.07 | KIR2DL4 | 8.78 |
| ITGA2 | 9.90 | TNF | 7.11 |
| TNF | 7.11 | TNFSF10 | 5.96 |
| HLA-DPB1 | 6.02 | KIR2DS5 | 4.70 |
| HLA-DQA1 | 5.96 | FAS | 3.64 |
| HLA-DQA2 | 4.58 | TNFRSF10B | 3.24 |
| CD9 | 4.51 | IFNG | 3.10 |
| CD3E | 4.48 | NCR3 | 2.78 |
| HLA-DMA | 3.95 | CASP3 | 2.65 |
| HLA-DRA | 3.81 | NRAS | 2.27 |
| HLA-DRB1 | 3.60 | ULBP3 | 2.21 |
| HLA-DQB1 | 3.47 | SH2D1A | 2.20 |
| HLA-DPA1 | 3.41 | PIK3R3 | 2.03 |
| HLA-DMB | 3.38 | FCER1G | 2.01 |
| TFRC | 3.16 | FASLG | 2.00 |
| CD59 | 3.14 | HCST | 1.90 |
| ITGA3 | 2.21 | TYROBP | 1.80 |
| IL4R | 1.51 | MICB | 1.80 |
| CR1 | −1.64 | KRAS | 1.72 |
| ITGA2B | −1.65 | FCGR3B | 1.69 |
| CD14 | −1.66 | FCGR3A | 1.64 |
| CD1C | −1.69 | GZMB | 1.60 |
| HLA-DRB5 | −1.74 | RAC1 | 1.56 |
| CSF2RA | −1.81 | RAC2 | 1.54 |
| CD7 | −1.82 | BID | 1.54 |
| CD36 | −1.86 | SOS1 | 1.53 |
| ITGB3 | −1.94 | KLRC1 | 1.53 |
| ANPEP | −2.02 | FYN | −1.51 |
| ITGA5 | −2.07 | SH3BP2 | −1.57 |
| IL3RA | −2.12 | PPP3R2 | −1.58 |
| CSF1R | −2.66 | HLA-C | −1.61 |
| CD38 | −3.21 | ZAP70 | −1.92 |
| ITGA6 | −3.64 | VAV3 | −1.94 |
| KIT | −4.83 | NFATC2 | −1.96 |
| IL7R | −30.21 | NFATC1 | −2.26 |
| | | ICAM2 | −4.38 |
| | | IFNGR2 | −4.85 |

Example 8: Measurement of Cancer Cell Killing Potential of Natural Killer Cells

As a result of examining through the above examples, since the proliferation potential and activity of natural killer cells induced by reprogramming from PBMC (CD34⁻ CD56⁻) cells isolated from peripheral blood mononuclear cells using reprogramming factors were excellent, the killing potential for various cancer cells was measured using the natural killer cells.

Specifically, as in Example 1, cells whose lineage had been converted, which were induced by NKIM-I medium, were cultured in NKIM-II for 14 or 35 days to measure the cancer cell killing potential of natural killer cells.

After diluting the cancer cells in DMEM medium including 10% fetal bovine serum each to be at 1×10⁵ cells/mL, Calcein-AM was added to be 25 μM, and cells washed with DMEM medium after culturing for one hour at 37° C. were used as Calcein-labeled target cells.

Example 8-1: Measurement of Cancer Cell Killing Potential Against Various Cancer Cells Using various tumor cells as target cells, cancer cell killing potential of the natural killer cells produced in the present invention was measured (Table 3).

TABLE 3

| No | Type of cancer | | Name of cell line | Ratio of target cell to NK (E:T) |
|---|---|---|---|---|
| 1 | Chronic myelogenous leukemia | Blood cancer | K562 | 0.25:1, 1:1, 2.5:1 |
| | Acute monocytic leukemia | Blood cancer | THP-1 | 0.25:1, 1:1, 2.5:1 |
| 2 | Glioblastoma | Brain cancer | U373MG | 0.25:1, 1:1, 2.5:1 |
| | Neuroblastoma | Brain cancer | SK-N-BE(2) | 0.25:1, 1:1, 2.5:1 |
| 3 | Hepatocellular carcinoma | Liver cancer | HepG2 | 0.25:1, 1:1, 2.5:1 |
| | Hepatocellular carcinoma | Liver cancer | Hep3B | 0.25:1, 1:1, 2.5:1 |

TABLE 3-continued

| No | Type of cancer | | Name of cell line | Ratio of target cell to NK (E:T) |
|---|---|---|---|---|
| 4 | Pancreas carcinoma | Pancreatic cancer | MIA PaCa-2 | 0.25:1, 1:1, 2.5:1 |
| 5 | Large cell lung cancer | Lung cancer | NCI-H460 | 0.25:1, 1:1, 2.5:1 |
| 6 | Ovary: ascites | Ovarian cancer | SK-OV-3 | 0.25:1, 1:1, 2.5:1 |
| 7 | Breast cancer cell | Breast cancer | MCF-7 | 0.25:1, 1:1, 2.5:1 |
|   | Breast cancer cell | Breast cancer | SK-BR-3 | 0.25:1, 1:1, 2.5:1 |
| 8 | Colon, colorectal adenocarcinoma, Dukes' type C | Colon cancer | SW620 | 0.25:1, 1:1, 2.5:1 |
|   | Colon, colorectal carcinoma | Colon cancer | HCT116 | 0.25:1, 1:1, 2.5:1 |
|   | Colon, colorectal adenocarcinoma, Dukes' type B | Colon cancer | SW480 | 0.25:1, 1:1, 2.5:1 |

Natural killer cells were prepared by diluting with NKIM-II at a cell number density of $0.25 \times 10^5$ cells/mL, $1 \times 10^5$ cells/mL, and $2.5 \times 10^5$ cells/mL, respectively, and then dispensed by 100 µL each into a 96-well culture plate. The prepared Calcein-labeled target cells ($1 \times 10^5$ cells/mL) were added to 96-well plates at 100 µL/well, and centrifuged at 400 g for 1 minute, and cultured in a cell incubator at 37° C. for 5 hours in the presence of 5% CO2. Then, 100 µL of the supernatant was taken from each well and measured with a fluorescence plate reader (485 nm/535 nm). The cell killing potential (%) was calculated according to the following formula.

Cancer cell killing potential (%)=(Measured value−Minimum value)/(Maximum value−Minimum value)×100

In the above formula, the minimum value is a measurement value of wells in which only Calcein-labeled target cells are present, and the maximum value is a measurement value of wells in which cells are completely lysed by adding 0.1% TritonX-100 to Calcein-labeled target cells.

As a result, it was confirmed to possess high killing potential against various cancer cells (FIG. 10).

Example 8-2: Comparative Experiment of Cancer Cell Killing Potential of Natural Killer Cells of the Present Invention and Existing Natural Killer Cells In order to confirm the excellent of the cancer cell killing potential of the natural killer cells produced in the present invention, a comparative experiment with existing human natural killer cells was performed.

Specifically, the cancer cell abilities of natural killer cells (experimental group) induced by culturing cells that were induced by NKIM-I medium, in which lineage had been converted, in NKIM-II medium for 28 days as in Example 1, and existing NK92 human natural killer cells (ATCC) (control group) against K562 and HepG2 cancer cells were evaluated by the measurement method of the cell killing potential using Calcein-AM as in Example 7-1.

As a result, it was confirmed that the cancer cell killing potential of the experimental group was about 3.8 to 5.8 times higher than that of the control group.

Example 8-3: Verification of Killing Potential Against Cancer Stem Cells and In Vivo Effect of Natural Killer Cells of the Present Invention In order to confirm the excellence of the killing potential of the natural killer cells produced in the present invention against cancer stem cells as well as the cancer cell killing potential, a comparative experiment of cancer cells and cancer stem cells was performed.

In order to proliferate and culture cancer stem cells from two types of colon cancer cells, SW620 and HCT116 other than blood cancer (K562) and liver cancer (HepG2) tested in Example 8-2, 10,000 cells were plated on a 35 mm culture dish and suspended and cultured in serum-free culture medium of 97% DMEM/F12, 1% penicillin/streptomycin, 10 ng/ml bFGF, 20 ng/ml EGF, and 2% B27 (*Sci Rep.* 2014 Dec. 15; 4:7481). The suspended and cultured cells were cultured to form a three-dimensional spheroid structure, and cultured by adding ½ of the existing culture solution every three to four days. The spheroids cultured for seven to ten days were recovered by centrifugation at 1,000 rpm for 5 minutes for passage culture, and treated with trypsin/EDTA to dissociate into single cells, and then the single cells were suspended and cultured in the culture medium.

Cancer stem cells that were proliferated from colon cancer cells were confirmed by analyzing the expression of CD133, a representative cancer stem cell marker, by flow cytometry (FACS).

As a result, it was confirmed that cancer stem cells were obtained, in which 79.5% and 80.4% of the cell group were CD133+, in the cell groups having undergone the culture process of cancer stem cells, from the SW620 cells and HCT116 cells.

As a result of measuring the expression of CD107a, as an indicator of killing potential after reacting induced natural killer cells and each of SW620, HCT116 cancer cells, and induced natural killer cells and each of SW620 and HCT116 cancer stem cells at a ratio of 1:1 for four hours, by flow cytometry (FACS), it was confirmed that the natural killer cells induced by each of SW620 and cancer stem cells exhibited 6.8% and 12.8% expressions, respectively, and showed high expression against cancer stem cells. Induced natural killer cells exhibited 4.7% and 8.6% expressions against HCT116 cancer cells and cancer stem cells, respectively, and showed high expression for cancer stem cells. Through this, it was found that induced natural killer cells have high killing potential against cancer stem cells (FIGS. 12A and 12B).

In addition, in vivo experiments were performed using mice to verify the anti-cancer effect of induced natural killer cells. The day after subcutaneous injection of $2 \times 10^6$ Sw620 into the back of 8-week-old nude mice (Balb/c-nude mouse, average weight 20 g to 25 g), induced natural killer cells ($5 \times 10^6$, $1.5 \times 10^7$) and 2 mg/kg of doxorubicin were injected. Induced natural killer cells were injected intravenously (i.v.) twice on D1 and D4, and doxorubicin was injected intraperitoneally (i.p) every two days (every other day) for two weeks. On the 28$^{th}$ day, the mice of each group were sacrificed by cervical dislocation technique, and the protruding cancer masses formed under the skin of the mice of each group were extracted. The extracted Sw620 cancer was compared by group to confirm the anti-cancer effect of induced natural killer cells (FIG. 13A).

As a result of comparing each group (PBS, iNK500 iNK1500, and doxorubicin) by subcutaneous injection of SW620, on day 28, it was confirmed that compared to the tumor size (1,369 mm$^3$) formed under the condition of injecting PBS, tumors of mice injected with induced natural killer cells [iNK500 ($5\times10^6$)—262 mm$^3$, iNK1500 ($1.5\times10^7$)—183 mm$^3$] were significantly reduced. In particular, it was confirmed that compared to the condition of injecting doxorubicin (262 mm$^3$), it showed a higher anti-cancer effect under the condition of injecting $1.5\times10^7$ induced natural killer cells (FIGS. 13B and 13C).

Example 8-4: Comparative Experiment of Cancer Cell Killing Potential of Natural Killer Cells of the Present Invention and Natural Killer Cells Derived from Umbilical Cord Blood In order to confirm the excellence of the cancer cell killing potential of natural killer cells produced in the present invention, a comparative experiment was performed with natural killer cells derived from umbilical cord blood.

Specifically, the cancer cell killing abilities of induced natural killer cells (experimental group) that were induced by culturing cells that were induced by NKIM-I medium as in Example 1, in which the lineage had been converted, for 28 days, and natural killer cells (ATCC) (control group) derived from umbilical cord blood against K562 and HepG2 cancer cells were evaluated by the measurement method of cell killing potential using Calcein-AM as in Example 7-1.

As a result, it was confirmed that the cancer cell killing potential of the natural killer cells of the present invention is about 1.4 to 2.13 times higher than that of the natural killer cells derived from umbilical cord blood (FIG. 14).

Example 9: Measurement of Cytokine Secretion Potential

The following experiment was performed to confirm the excellent of the cytokine secretion potential of natural killer cells produced in the present invention.

First, to obtain a conditioned medium, natural killer cells of $1\times10^5$ cells/mL 0.5 mL and the same cell concentration and same amount were mixed for various cancer cells as in Example 7, respectively. After 16 hours, 1 mL of the cultured solution was filtered using a 0.22 µm filter (Millipore). To measure the concentration of secreted cytokines (IFN-γ, Granzyme B, and TNF-α), ELISA was performed in the conditioned media derived from the control group (no target) and the experimental groups according to the manufacturer's protocol (Abcam).

As a result, it was confirmed that the cytokine secretion potential of the natural killer cells of the present invention is significantly superior to the existing NK92 human natural killer cells under co-culture conditions with K562 and HepG2 (FIG. 15A). In addition, it was confirmed that cytokine secretion was significantly promoted in co-culture conditions with various cancer cells, u373 mg, THP-1, A549, Hep3B, MCF7, etc. other than K562 and HepG2 cancer cells (FIG. 15B).

Example 10: Characteristics of Natural Killer Cells Induced Using Non-Integrative Episomal Vectors Unlike Examples 1 to 8 in which reprogramming vectors were introduced using a viral system, an experiment was performed to transform a reprogramming factor using a non-integrative episomal vector, which is another transporter of the reprogramming factor.

Specifically, after recovering PBMC-34-56 cells as in Example 1, with the protocol provided by the manufacturer using Neon® transfectionsystem (Invitrogen) at a cell number of $1\times10^6$, five reprogramming factors, hOCT3/4, hSOX2, hKLF4, hLIN28, and hL-MYC, and pCEP4 episomal vectors based on oriP/EBNA1 expressing shp53, which is a factor for promoting the efficiency of reprogramming, were transformed by setting the basic conditions of 1,650 V pulse voltage, 10 ms pulse width, and 3 pulse number by electroporation. The transformed cells were plated in 24-well culture plates and cultured in PBMC medium.

The next day, the cells were cultured for five days in NKIM-I medium (StemSpan SFEM II including 10% FBS, 1% Penicillin/Streptomycin, 5 µM CT99021, 20 ng/ml Human IL-3, 20 ng/ml Human IL-6, 20 ng/ml Human SCF, 20 ng/ml Human FLT3, 20 ng/ml Human TPO). On the 6$^{th}$ day of culture, after isolating formed colonies (cells whose lineage had been converted) produced in the culture, the isolated colonies were cultured for 14 days in NKIM-II medium (StemSpan SFEM II including 10% FBS, 1% Penicillin/Streptomycin, 25 ng/ml Human IL-2, 20 ng/ml Human IL-7 20 ng/ml Human IL-15, 20 ng/ml Human SCF, 20 ng/ml Human FLT3, 2 µM StemRegenin I) to induce to natural killer cells.

In order to confirm whether natural killer cells were produced through the direct reprogramming, as in Example 1, after staining with antibodies to CD56 and CD3 attached with fluorescence, the groups of natural killer cells (CD56+ and CD3−) were analyzed by flow cytometry.

As a result, in the case of the control group, whereas the cell group in which CD56, an indicator of natural killer cells was 0.8%, it was confirmed that 24.6% was the group of natural killer cells with CD56 positive (FIG. 16A).

In addition, to evaluate the cancer cell killing potential of natural killer cells induced using the episomal vector, the cell killing potential was evaluated by the measurement method using Calcein-AM as in Example 7-1, and as a result, it showed cancer cell killing potential of 40.32% or 49.23% for K562 or HepG2, respectively (FIG. 16B).

Through this, it was confirmed that natural killer cells induced by direct reprogramming could be produced using a non-integrative episomal vector without using a virus.

Example 11: Characteristics of Cryopreserved Induced Natural Killer Cells

Cryopreservation was performed to maintain long-term preservation and characteristics of induced natural killer cells, and in order to confirm that the characteristics of the induced natural killer cells were maintained upon thawing, a comparative experiment was performed with fresh induced natural killer cells.

In order to preserve the induced natural killer cells and maintain their characteristics, induced natural killer cells of $1\times10^8$ cells were stored in a cell vial for cryopreservation, which is 1 mL of Recovery™ cell culture cryopreservation medium. To verify the characteristics of cryopreserved induced natural killer cells, after thawing, the fresh induced natural killer cells and the expression patterns of cell surface receptors were compared and analyzed using flow cytometry (FACS).

As a result, by confirming that the expressions of CD56, CD16, CD69, DNAM-I, NKG2D, NKp46, etc. were similar in the fresh induced natural killer cells and cryopreserved induced natural killer cells, it was verified that the characteristics of cells did not change after cryopreservation (FIG. 17).

From the above description, those skilled in the art will appreciate that the present invention can be implemented in other specific forms without changing the technical spirit or essential features. In this regard, the embodiments described above are to be understood in all respects as illustrative and not restrictive. The scope of the present invention should be construed that all changes or modifications derived from the meaning and scope of the following claims and equivalent concepts rather than the detailed description are included in the scope of the present invention.

The invention claimed is:

1. A method for producing natural killer cells comprising directly reprogramming into natural killer cells, consisting of:
   (a) introducing a reprogramming factor into isolated cells, wherein the reprogramming factor is Oct4, Sox2, Klf4, and Myc; and
   (b) from the following day after the introduction, culturing the cells of step (a) in i) a first medium comprising cytokine, growth factor, and GSK3β inhibitor to increase the efficiency of direct reprogramming, and ii) a second medium comprising cytokine, growth factor, and aryl hydrocarbon receptor inhibitor to promote the production of natural killer cells, wherein the cytokine in the first medium is one or more selected from the group consisting of IL-2, IL-3, IL-6, IL-7, IL-11, IL-15, and IL-21; and the growth factor in the first medium comprises SCF (Stem Cell Factor), FLT3 (Fms-like Tyrosine Kinase 3) ligand, and TPO (Thrombopoietin) and is one or more selected from the group consisting of EPO (Erythropoietin), BMP4 (Bone Morphogenetic Protein 4), and EGF (Epidermal Growth Factor), wherein the cytokine in the second medium is one or more selected from the group consisting of IL-2, IL-7, and IL-15; and the growth factor in the second medium comprises SCF and FLT3 ligand,
   wherein the isolated cells are peripheral blood mononuclear cells, skin fibroblasts or dental pulp cells,
   wherein when the isolated cells are peripheral blood mononuclear cells, the first medium in step (b) includes IL-3, IL-6, SCF, FLT3, TPO, and CT 99021; and the second medium in step (b) includes IL-2, IL-7, IL-15, SCF, FLT3, and StemRegenin, wherein the peripheral blood mononuclear cells are further cultured in a medium including Serum-free medium supplement, Ascorbate, MTG (Monothioglycerol), L-glutamine, Human transferrin, SB431542, CT99021, IL-3, IL-6, IL-11, SCF, FLT3, TPO, and EPO before culturing in the second medium in step (b),
   wherein when the isolated cells are skin fibroblasts or dental pulp cells, the first medium in step (b) includes FBS, Serum Replacement, NEAA (Non-Essential Amino Acids), β-mercaptoethanol, bFGF (basic Fibroblast Growth Factor), and CT99021, and the second medium in step (b) includes IL-2, IL-7, IL-15, SCF, FLT3, and StemRegenin, and wherein the skin fibroblasts or dental pulp cells are further cultured in a (a') medium including Serum-free medium supplement, Ascorbate, MTG, L-glutamine, Human transferrin, SB431542, CT99021, IL-3, IL-6, IL-11, SCF, FLT3, TPO, and EPO, and then cultured in a (b') medium including N2, neuronal cell culture supplement, BSA (Bovine Serum Albumin), Ascorbate, MTG (Monothioglycerol), L-glutamine, Human transferrin, BMP4, bFGF, SB431542, and CT99021, before culturing in the second medium in step (b).

2. The method of claim 1, wherein the produced natural killer cells express CD56, CD16, or a combination thereof.

3. The method of claim 1, wherein the natural killer cells retain the characteristics of natural killer cells upon thawing after cryopreservation.

4. The method of claim 1, wherein the natural killer cells up-express a biomarker associated with hematopoietic cell lineage or natural killer cell-mediated cytotoxicity, compared to natural killer cells isolated from humans.

5. The method of claim 4, wherein the biomarker associated with the hematopoietic cell lineage is one or more selected from the group consisting of CSF1, ITGA2, TFRC, CD3e, TNF, M-SCF, CD59, and CD9.

6. The method of claim 4, wherein the biomarker associated with natural killer cell-mediated cytotoxicity is one or more selected from the group consisting of KIR2DL, KIR2DS, NKp30, FCER1G, ULBP3, SAP, TNFa, TNFSF10, IFNg, TRAIL, FAS, and CASP.

7. A method for producing a cell therapeutic agent comprising the natural killer cells as an active ingredient, the method comprising:
   (a) introducing a reprogramming factor into isolated cells, wherein the reprogramming factor is Oct4, Sox2, Klf4, and Myc; and
   (b) from the following day after the introduction, culturing the cells of step (a) in i) a first medium comprising cytokine, growth factor, and GSK3β inhibitor to increase the efficiency of direct reprogramming, and ii) a second medium comprising cytokine, growth factor, and aryl hydrocarbon receptor inhibitor to promote the production of natural killer cells, wherein the cytokine in the first medium is one or more selected from the group consisting of IL-2, IL-3, IL-6, IL-7, IL-11, IL-15, and IL-21; and the growth factor in the first medium comprises SCF (Stem Cell Factor), FLT3 (Fms-like Tyrosine Kinase 3) ligand, and TPO (Thrombopoietin) and is one or more selected from the group consisting of EPO (Erythropoietin), BMP4 (Bone Morphogenetic Protein 4), and EGF (Epidermal Growth Factor), wherein the cytokine in the second medium is one or more selected from the group consisting of IL-2, IL-7, and IL-15; and the growth factor in the second medium comprises SCF and FLT3 ligand,
   wherein the isolated cells are peripheral blood mononuclear cells, skin fibroblasts or dental pulp cells,
   wherein when the isolated cells are peripheral blood mononuclear cells, the first medium in step (b) includes IL-3, IL-6, SCF, FLT3, TPO, and CT 99021; and the second medium in step (b) includes IL-2, IL-7, IL-15, SCF, FLT3, and StemRegenin, wherein the peripheral blood mononuclear cells are further cultured in a medium including Serum-free medium supplement, Ascorbate, MTG (Monothioglycerol), L-glutamine, Human transferrin, SB431542, CT99021, IL-3, IL-6, IL-11, SCF, FLT3, TPO, and EPO before culturing in the second medium in step (b),
   wherein when the isolated cells are skin fibroblasts or dental pulp cells, the first medium in step (b) includes FBS, Serum Replacement, NEAA (Non-Essential Amino Acids), β-mercaptoethanol, bFGF (basic Fibroblast Growth Factor), and CT99021, and the second medium in step (b) includes IL-2, IL-7, IL-15, SCF, FLT3, and StemRegenin, and wherein the skin fibroblasts or dental pulp cells are further cultured in a (a') medium including Serum-free medium supplement, Ascorbate, MTG (Monothioglycerol), L-glutamine, Human transferrin, SB431542, CT99021, IL-3, IL-6, IL-11, SCF, FLT3, TPO, and EPO, and then cultured in a (b') medium including N2, neuronal cell culture supplement, BSA (Bovine Serum Albumin), Ascorbate, MTG (Monothioglycerol), L-glutamine, Human transferrin, BMP4, bFGF, SB431542, and CT99021, before culturing in the second medium in step (b), (c) isolating the natural killer cells from the cultured cells of step (b); and (d) formulating the isolated natural killer cells into a cell therapeutic agent.

8. A method for producing a pharmaceutical composition for treating or preventing cancer, the method comprising:
  (a) introducing a reprogramming factor into isolated cells, wherein the reprogramming factor is Oct4, Sox2, Klf4, and Myc; and
  (b) from the following day after the introduction, culturing the cells of step (a) in i) a first medium comprising cytokine, growth factor, and GSK3β inhibitor to increase the efficiency of direct reprogramming, and ii) a second medium comprising cytokine, growth factor, and aryl hydrocarbon receptor inhibitor to promote the production of natural killer cells, wherein the cytokine in the first medium is one or more selected from the group consisting of IL-2, IL-3, IL-6, IL-7, IL-11, IL-15, and IL-21; and the growth factor in the first medium comprises SCF (Stem Cell Factor), FLT3 (Fms-like Tyrosine Kinase 3) ligand, and TPO (Thrombopoietin) and is one or more selected from the group consisting of EPO (Erythropoietin), BMP4 (Bone Morphogenetic Protein 4), and EGF (Epidermal Growth Factor), wherein the cytokine in the second medium is one or more selected from the group consisting of IL-2, IL-7, and IL-15; and the growth factor in the second medium comprises SCF and FLT3 ligand,
  wherein the isolated cells are peripheral blood mononuclear cells, skin fibroblasts or dental pulp cells,
  wherein when the isolated cells are peripheral blood mononuclear cells, the first medium in step (b) includes IL-3, IL-6, SCF, FLT3, TPO, and CT 99021; and the second medium in step (b) includes IL-2, IL-7, IL-15, SCF, FLT3, and StemRegenin, wherein the peripheral blood mononuclear cells are further cultured in a medium including Serum-free medium supplement, Ascorbate, MTG (Monothioglycerol), L-glutamine, Human transferrin, SB431542, CT99021, IL-3, IL-6, IL-11, SCF, FLT3, TPO, and EPO before culturing in the second medium in step (b),
  wherein when the isolated cells are skin fibroblasts or dental pulp cells, the first medium in step (b) includes FBS, Serum Replacement, NEAA (Non-Essential Amino Acids), β-mercaptoethanol, bFGF (basic Fibroblast Growth Factor), and CT99021, and the second medium in step (b) includes IL-2, IL-7, IL-15, SCF, FLT3, and StemRegenin, and wherein the skin fibroblasts or dental pulp cells are further cultured in a (a') medium including Serum-free medium supplement, Ascorbate, MTG, L-glutamine, Human transferrin, SB431542, CT99021, IL-3, IL-6, IL-11, SCF, FLT3, TPO, and EPO, and then cultured in a (b') medium including N2, neuronal cell culture supplement, BSA (Bovine Serum Albumin), Ascorbate, MTG (Monothioglycerol), L-glutamine, Human transferrin, BMP4, bFGF, SB431542, and CT99021, before culturing in the second medium in step (b), (c) isolating the natural killer cells from the cultured cells of step (b); and (d) mixing the isolated natural killer cells with a pharmaceutically acceptable salt to formulate the pharmaceutical composition.

9. The method of claim 8, wherein the cancer is pancreatic cancer, lung cancer, ovarian cancer, breast cancer, colorectal cancer, bone marrow cancer, liver cancer, brain cancer, prostate cancer, stomach cancer, colon cancer, glioma, melanoma, lymphoma, rectal cancer, blood cancer, or a combination thereof.

10. The method of claim 8, wherein the composition has a potential for killing cancer stem cells.

11. A method for producing natural killer cells, which are capable of maintaining the characteristics of natural killer cells even when they are thawed after cryopreservation, comprising directly reprogramming into natural killer cells, consisting of:
  (a) introducing a reprogramming factor into isolated cells, wherein the reprogramming factor is Oct4, Sox2, Klf4, and Myc; and
  (b) from the following day after the introduction, culturing the cells of step (a) in i) a first medium comprising cytokine, growth factor, and GSK3β inhibitor to increase the efficiency of direct reprogramming, and ii) a second medium comprising cytokine, growth factor, and aryl hydrocarbon receptor inhibitor to promote the production of natural killer cells, wherein the cytokine in the first medium is one or more selected from the group consisting of IL-2, IL-3, IL-6, IL-7, IL-11, IL-15, and IL-21; and the growth factor in the first medium comprises SCF, FLT3 ligand, and TPO and is one or more selected from the group consisting of EPO, BMP4, and EGF, wherein the cytokine in the second medium is one or more selected from the group consisting of IL-2, IL-7, and IL-15; and the growth factor in the second medium comprises SCF and FLT3 ligand,
  wherein the isolated cells are peripheral blood mononuclear cells, skin fibroblasts or dental pulp cells,
  wherein when the isolated cells are peripheral blood mononuclear cells, the first medium in step (b) includes IL-3, IL-6, SCF, FLT3, TPO, and CT 99021; and the second medium in step (b) includes IL-2, IL-7, IL-15, SCF, FLT3, and StemRegenin, wherein the peripheral blood mononuclear cells are further cultured in a medium including Serum-free medium supplement, Ascorbate, MTG, L-glutamine, Human transferrin, SB431542, CT99021, IL-3, IL-6, IL-11, SCF, FLT3, TPO, and EPO before culturing in the second medium in step (b),
  wherein when the isolated cells are skin fibroblasts or dental pulp cells, the first medium in step (b) includes FBS, Serum Replacement, NEAA, β-mercaptoethanol, bFGF, and CT99021, and the second medium in step (b) includes IL-2, IL-7, IL-15, SCF, FLT3, and StemRegenin, and wherein the skin fibroblasts or dental pulp cells are further cultured in a (a') medium including Serum-free medium supplement, Ascorbate, MTG, L-glutamine, Human transferrin, SB431542, CT99021, IL-3, IL-6, IL-11, SCF, FLT3, TPO, and EPO, and then cultured in a (b') medium including N2, neuronal cell culture supplement, BSA, Ascorbate, MTG, L-glutamine, Human transferrin, BMP4, bFGF, SB431542, and CT99021, before culturing in the second medium in step (b).

\* \* \* \* \*